(12) United States Patent
Tanaka et al.

(10) Patent No.: US 8,119,081 B2
(45) Date of Patent: Feb. 21, 2012

(54) SPECIMEN ANALYSIS APPARATUS AND SPECIMEN ANALYSIS METHOD

(75) Inventors: Yousuke Tanaka, Kobe (JP); Masayuki Ikeda, Kobe (JP); Takamichi Naito, Kobe (JP)

(73) Assignee: Sysmex Corporation, Kobe (JP)

( * ) Notice: Subject to any disclaimer, the term of this patent is extended or adjusted under 35 U.S.C. 154(b) by 1079 days.

(21) Appl. No.: 11/729,017

(22) Filed: Mar. 28, 2007

(65) Prior Publication Data

US 2007/0231208 A1  Oct. 4, 2007

(30) Foreign Application Priority Data

Mar. 31, 2006 (JP) ................. 2006-096943

(51) Int. Cl.
*B01L 3/02* (2006.01)
(52) U.S. Cl. ............ 422/510; 422/63; 422/65; 422/501; 422/509
(58) Field of Classification Search .............. 422/63–67, 422/99, 100, 102, 501, 509, 510; 436/43, 436/47–49
See application file for complete search history.

(56) References Cited

U.S. PATENT DOCUMENTS

2004/0096931 A1* 5/2004 Kawashima et al. ........... 435/34

FOREIGN PATENT DOCUMENTS

| EP | 0387787 A2 | 9/1990 |
|---|---|---|
| EP | 1063527 A2 | 12/2000 |
| JP | 61-110060 | 5/1986 |
| JP | 2-195260 | 8/1990 |
| JP | H5-151282 | 6/1993 |
| JP | 6-249858 | 9/1994 |
| JP | 10-96688 | 4/1998 |
| JP | 2000-283985 | 10/2000 |

OTHER PUBLICATIONS

European Search Report for Application No. EP 07006744 dated Jul. 11, 2007.
Haeckel, R. "Proposals for the Description and Measurement of Carry-Over Effects in Clinical Chemistry," *Pure & Appl. Chem.*, 1991, 63(2), pp. 301-306.

* cited by examiner

*Primary Examiner* — Jill Warden
*Assistant Examiner* — Dwayne K Handy
(74) *Attorney, Agent, or Firm* — Brinks Hofer Gilson & Lione

(57) ABSTRACT

A specimen analysis method, comprising: bringing a first specimen vessel to a sucking position for sucking specimens; obtaining a first measurement result of a first specimen contained in the first specimen vessel; bringing a second specimen vessel to the sucking position before the first measurement result is obtained; obtaining a second measurement result of a second specimen contained in the second specimen vessel; bringing a third specimen vessel to the sucking position after the first measurement result is obtained; obtaining a third measurement result of a third specimen contained in the third specimen vessel; and obtaining a fourth measurement result of the second specimen when the first measurement result is higher than a threshold, the second specimen being sucked at the sucking position again for obtaining the fourth measurement result before bringing the third specimen vessel to the sucking position, is disclosed. A specimen analysis is also disclosed.

9 Claims, 29 Drawing Sheets

FIG. 23

| | | | | 325d | 325e | 324 | 325f |

Progress State Screen (Specimen Progress State Confirmation Screen)

| | | | | | | Measurement Initiation |

Progress State

Specimen Progress State | Status of use of all racks

322

| Rack 1 in Measurement | Rack 2 | Rack 3 | Rack 4 | Rack 5 | | Emergency Rack |

323 — Specimen Number | CEA ng/mL | FRN ng/mL | HBsAg U/mL | TP SU/mL | STS SU/mL | HBsAb mU/mL

| # | Specimen No. | Type | | Value | | | |
|---|---|---|---|---|---|---|---|
| 1 | 122366 | S | | *B***** | | | |
| 2 | MHHDIJI | S | | >56.00 | | | |
| 3 | 652 | S | OB*** | 1.30/+- | | | |
| 4 | 45655 | WB | | 5.58/- | | | |
| 5 | 655-335 | S | | 10.55/- | | | |
| 6 | 655-336 | S | | >20.91 | | | |
| 7 | 655-337 | S | | 8.98 | | | |
| 8 | 00-000000001 | S | | 19.78 | | | |
| 9 | 00-000000003 | S | O | - | | | |
| 10 | | | | | | | |

325a, 325b, 325c, 326a, 326b, 326c, 326d

Main Menu

321 — | Measurement Registration | Stored Specimens | Precision Control | Calibration Curve | Maintenance | Setting | Plate Exchange | | Shut Down |

326

SPECIMEN ANALYSIS APPARATUS AND SPECIMEN ANALYSIS METHOD

RELATED APPLICATIONS

This application claims priority under 35 U.S.C. §119 to Japanese Patent Application No. JP2006-096943 filed Mar. 31, 2006, the entire content of which is hereby incorporated by reference.

FIELD OF THE INVENTION

The present invention relates to a specimen analysis apparatus and specimen analysis method. More specifically, the invention relates to a specimen analysis apparatus and specimen analysis method used in analyzing components in a specimen such as blood or urine sampled from a patient in order to discover a disease or estimate an abnormal site.

BACKGROUND OF THE INVENTION

In inspection departments, inspection centers, etc. of hospitals, a variety of inspections are conducted using specimens such as blood and urine sampled from patients in order to discover diseases or estimate abnormal sites. Recently, automatic inspection (analysis) apparatuses are used for labor saving and speed-up of inspections.

For example, methods of analyzing concrete components in urine include a method of irradiate a urine specimen by flow cytometry and then classifying concrete components in urine into white blood cells, red blood cells, epithelial cells, cylinder and bacteria, on the basis of the resulting scattered light and fluorescence (see Japanese Laid-Open Patent Publication No. H05-151282).

In such a automatic analysis apparatus, a plurality of specimens pass through a sample preparation section of mixing a specimen with a reagent to prepare a measurement sample and a specimen passage channel including a measurement section of measuring the measurement sample, so the specimen passage channel is washed for every completion of each measurement using a washing solution such as a reagent and a dilution solution in order that remaining of a previously measured specimen in the specimen passage channel (carry-over) is restrained to guarantee measurement precision and reliability. This washing operation is normally for a specified washing time and in a specified amount of a washing solution to restrain carry-over within a predetermined value. However, there is a specimen of being a target for analysis, the concentration of which is as very high as tens of thousands times a normal value (a high value specimen). If such a high value specimen is washed for the same washing time and in the same amount of a washing solution as in a normal specimen, the washing becomes insufficient and carry-over occurs in a next specimen. This poses the problem of not obtaining a precise measurement value.

Thus, proposed is an apparatus of automatically adjusting the washing time and/or the amount of a washing solution of the specimen passage channel in accordance with the number of the particles of the measured specimens (see Japanese Laid-Open Patent Publication No. H10-096688). The apparatus disclosed in this Japanese Laid-Open Patent Publication No. H10-096688 is configured so that washing conditions are set after completion of specimen measurement and then the processing proceeds to a next specimen after carrying out washing operation.

Recently, there is increasing demand for speed-up for a variety of inspections in order to achieve speedy diagnosis and treatment as well as improve management efficiency of medical institutions. However, where the setting of washing conditions and the execution of washing operation are done after completion of specimen measurement and then further the next specimen is processed like the apparatus described in Japanese Laid-Open Patent Publication No. H10-096688, speed-up of analysis is limited and the needs of the time cannot be met.

SUMMARY OF THE INVENTION

The scope of the present invention is defined solely by the appended claims, and is not affected to any degree by the statements within this summary.

A first aspect of the present invention is a specimen analysis apparatus for analyzing a component contained in a specimen, comprising:

a specimen suction section for sucking a specimen from a specimen vessel placed on a specimen vessel placing section;

a sample preparation section for preparing a measurement sample by mixing the specimen sucked by the specimen suction section with a reagent;

a measurement section for measuring a component in the measurement sample;

a first control means for controlling operations of the specimen suction section, the sample preparation section and the measurement section to implement processing of a first specimen;

a second control means for controlling operations of the specimen suction section, the sample preparation section and the measurement section to initiate processing of a second specimen different from the first specimen during the implementation of the processing of the first specimen by the first control means;

a judge means for judging whether a measurement result of the first specimen exceeds a threshold; and a third control means for controlling operations of the specimen suction section, the sample preparation section and the measurement section to implement the reprocessing of the second specimen when the judge means judges that the measurement result of the first specimen exceeds the threshold.

A second aspect of the present invention is a specimen analysis apparatus for analyzing a component contained in a specimen, comprising:

a specimen suction section for sucking a specimen from a specimen vessel placed on a specimen vessel placing section;

a sample preparation section for preparing a measurement sample by mixing the specimen sucked by the specimen suction section with a reagent;

a measurement section for measuring a component in the measurement sample;

a display;

a first control means for controlling operations of the specimen suction section, the sample preparation section and the measurement section to implement processing of a first specimen;

a second control means for controlling operations of the specimen suction section, the sample preparation section and the measurement section to initiate processing of a second specimen different from the first specimen during the implementation of the processing of the first specimen by the first control means;

a judge means for judging whether a measurement result of the first specimen exceeds a threshold; and a display control means for controlling the display so as to display notice for remeasurement of the second specimen when the judge means judges that the measurement result of the first specimen exceeds the threshold.

A third aspect of the present invention is a specimen analysis apparatus for analyzing a component contained in a specimen, comprising:

a specimen vessel placing section on which a plurality of specimen vessels are capable of being placed;

a specimen suction section for sucking a specimen from a specimen vessel placed on the specimen vessel placing section;

a sample preparation section for preparing a measurement sample by mixing the specimen sucked by the specimen suction section with a reagent;

a measurement section for measuring a component in the measurement sample;

a cleaning section for cleaning a specimen passage channel through which a specimen passes; and a controller for controlling operations of the specimen suction section, the sample preparation section and the measurement section to implement processing of the specimen, the processing comprising suction of a specimen, preparation of a measurement sample and measurement of a component in the measurement sample, wherein the controller is configured so as to initiate processing of a next specimen during processing of a previous specimen and, when measurement result of the previous specimen exceeds a threshold, implement reprocessing of the next specimen.

A fourth aspect of the present invention is a specimen analysis apparatus for analyzing a component contained in a specimen, comprising:

a specimen vessel placing section on which a plurality of specimen vessels are capable of being placed;

a specimen suction section for sucking a specimen from a specimen vessel placed on the specimen vessel placing section;

a sample preparation section for preparing a measurement sample by mixing the specimen sucked by the specimen suction section with a reagent;

a measurement section for measuring a component in the measurement sample;

a cleaning section for cleaning a specimen passage channel through which a specimen passes; a display; and a controller for controlling operations of the specimen suction section, the sample preparation section and the measurement section to implement processing of the specimen, the processing comprising suction of a specimen, preparation of a measurement sample and measurement of a component in the measurement sample, wherein the control section is configured so as to initiate processing of a next specimen during processing of a previous specimen and, when measurement result of the previous specimen exceeds a threshold, control the display so as to display notice for reprocessing of the next specimen.

A fifth aspect of the present invention is a specimen analysis method, comprising:

bringing a first specimen vessel to a sucking position for sucking specimens;

obtaining a first measurement result of a first specimen contained in the first specimen vessel;

bringing a second specimen vessel to the sucking position before the first measurement result is obtained;

obtaining a second measurement result of a second specimen contained in the second specimen vessel;

bringing a third specimen vessel to the sucking position after the first measurement result is obtained;

obtaining a third measurement result of a third specimen contained in the third specimen vessel; and obtaining a fourth measurement result of the second specimen when the first measurement result is higher than a threshold, the second specimen being sucked at the sucking position again for obtaining the fourth measurement result before bringing the third specimen vessel to the sucking position.

BRIEF DESCRIPTION OF THE DRAWINGS

FIG. 23 is a diagram indicating a progress status screen (specimen progress status confirmation screen) displayed on a display section of the immune aggregation measurement apparatus according to the embodiment indicated in FIG. 16.

DESCRIPTION OF THE PREFERRED EMBODIMENTS

An embodiment of a specimen analysis apparatus will be set forth in detail in reference with the appended drawings hereinafter.

Figure 1:
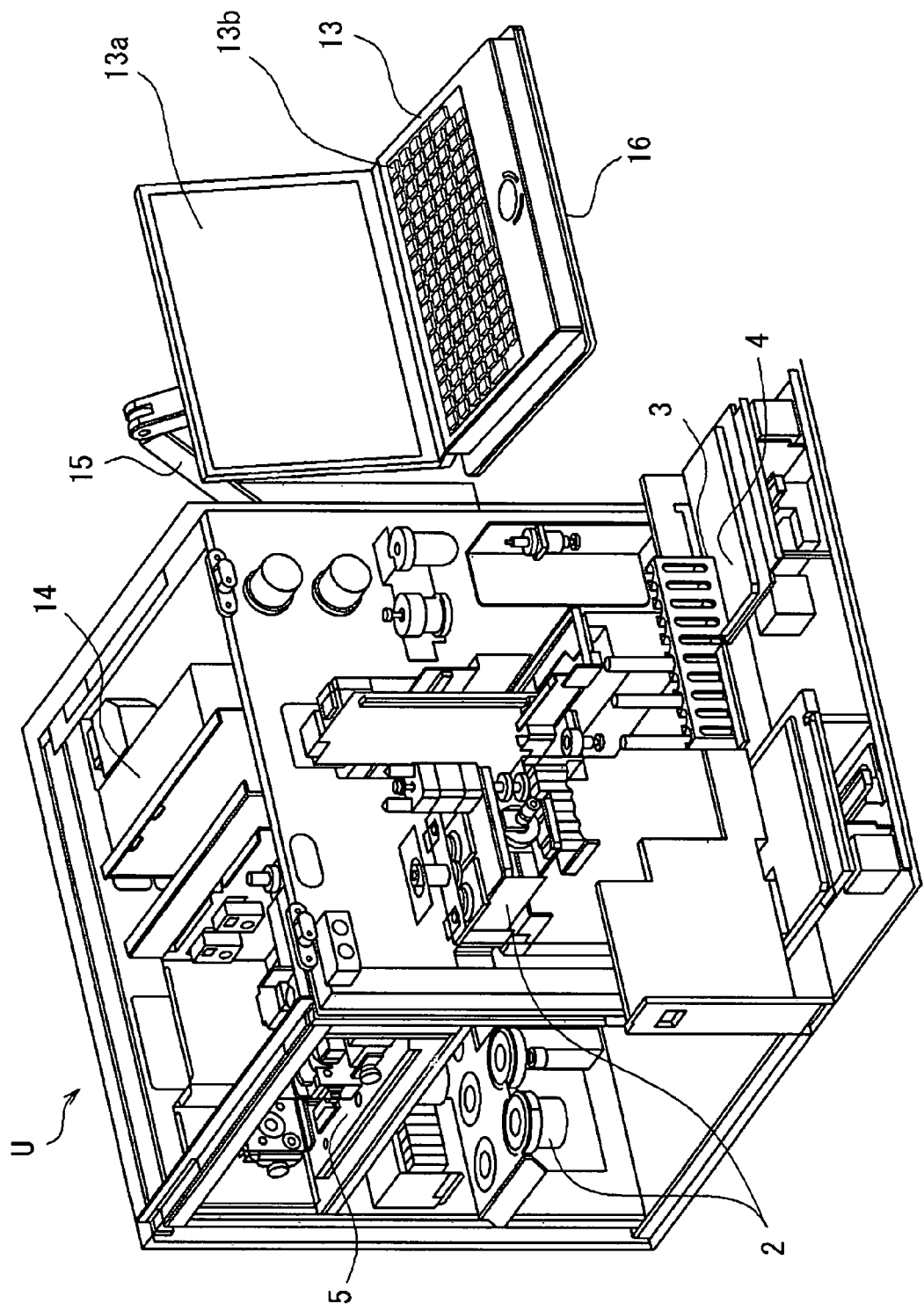
FIG. 1 is a perspective depiction view of a urine analysis apparatus, an embodiment of a specimen analysis apparatus of the present invention.

FIG. 1 is a perspective depiction view of a specimen analysis apparatus according to one embodiment of the present invention. Additionally, in FIG. 1, a basket body accommodating constituents of the specimen analysis apparatus is partially omitted for easy understanding.

[Configuration of Apparatus]

In FIG. 1, a urine analysis apparatus U of being a specimen analysis apparatus includes a sample preparation section 2 of preparing a sample transporting a sample rack (test tube stand) 3, a rack table 4 of being a specimen vessel mounting section, an optical detection section 5 for detecting information of concrete components and bacteria in urine from a measurement sample, and a circuit section 14. The side face of the basket body is equipped with base 16 via an arm 15, with a computer 13 being set on the base. The computer 13 is LAN connected to the circuit section 14 of the urine analysis apparatus U.

In the embodiment, a measurement section of measuring a clinical specimen of a patient is mainly constituted by the optical detection section 5 and the circuit section 14; an output section of outputting measurement results by the measurement section is constituted by the computer 13 and a display 13a.

Figure 2:
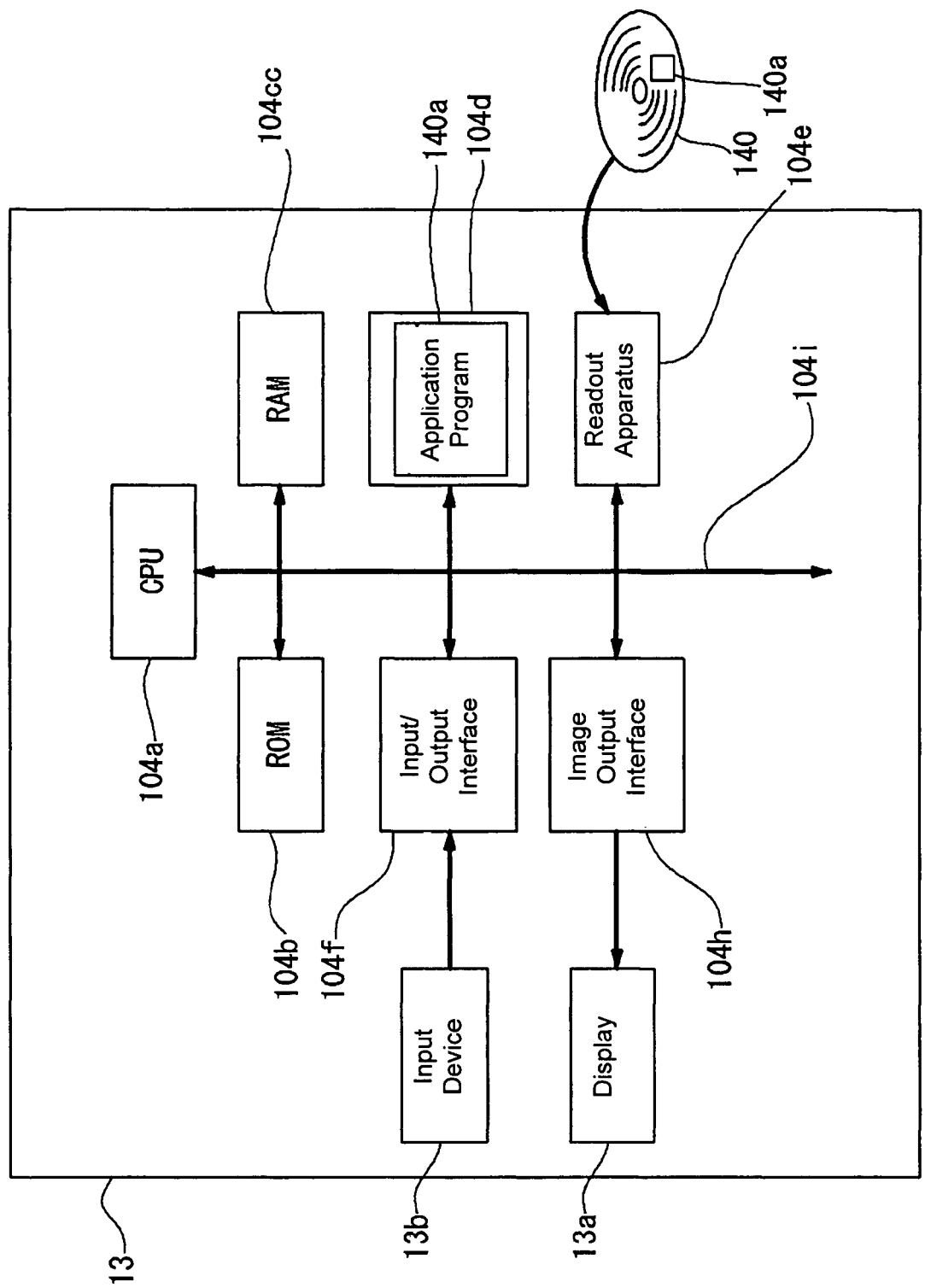
FIG. 2 is a block diagram indicating a hardware configuration of the computer indicated in FIG. 1.

The computer 13 includes the following constituents in more detail. As indicated in FIG. 2, the computer 13 includes a CPU 104a, a ROM 104b, a RAM 104c, a hard disk 104d, a readout device 104e, an input and output interface 104f, a communication interface 104g and an image output interface 104h; the CPU 104a, the ROM 104b, the RAM 104c, the hard disk 104d, the readout device 104e, the input and output interface 104f and an image output interface 104h are connected to a bus 104i in a communication possible fashion.

The CPU 104a is capable of executing a computer program stored in the ROM 104b and a computer program loaded in the RAM 104c. Execution of an application program 140a as discussed later by the CPU 104a renders the computer 13 to serve as a system.

The ROM 104b is constituted by a masked ROM, a PROM, an EPROM, an EEPROM, and others, and records a computer program executed in the CPU 104a and data and the like used therefor.

The RAM 104c is constituted by a SRAM or a DRAM or the like. The RAM 104c is used in readout of a computer program recorded in the ROM 104b and the hard disk 104d. Additionally, the RAM 104c is utilized as an operation area of the CPU 104a when these computer programs are executed.

The hard disk 104d has installed therein a variety of computer programs such as an operating system and application programs for causing the CPU 104a to execute. An application program 140a as described later is also installed in this hard disk 104d.

The readout device 104e is constituted by a flexible disk drive, a CD-ROM drive, a DVD-ROM drive, or the like, and can read out a computer program or data recorded in a portable recording medium 140. In addition, the portable recording medium 140 accommodates the application program 140a for rendering the computer 13 to function as a system of the present invention. This makes it possible to cause the computer 13 to read out the application program 140a according to the present invention from the portable recording medium 140 and to install the application program 140a in the hard disk 104d.

The application program 140a can not only be provided by the portable recording medium 140, but also be provided through an electric communication line from an outer instrument connected to the computer 13 in a communication possible fashion by means of the electric communication line (whether it is a wired system or wireless system). For example, the application program 140a is accommodated within a hard disk of a sever computer on Internet. It is also possible that to this server computer is accessed the computer 13 to download the computer program, which is installed in the hard disk 104d.

Additionally, the hard disk 104d has installed therein, for example an operating system that provides graphical user interface environment such as Windows (trade name) available from Microsoft Corporation, USA. In the descriptions that follow, the application program 140a according to the embodiment is regarded as operating on the operating system.

The input and output interface 104f is constituted by, for example, serial interfaces such as a USB, IEEE1394 and RS-232C, parallel interfaces such as a SCSI, IDE and IEEE1284, analog interfaces made from a D/A converter and A/D converter, and others. To the input and output interface 104f is connected an input device (input unit) 13b made from a key board, mouse, and others; the use of the input device 13b by a user enables the input of data in the computer 13.

An image output interface 104h is connected to the display 13a constituted by an LCD, CRT or the like, and outputs on the display 13a image signals according to image data given from the CPU 104a. The display 13a displays an image (screen) based on video signals inputted.

Figure 3:
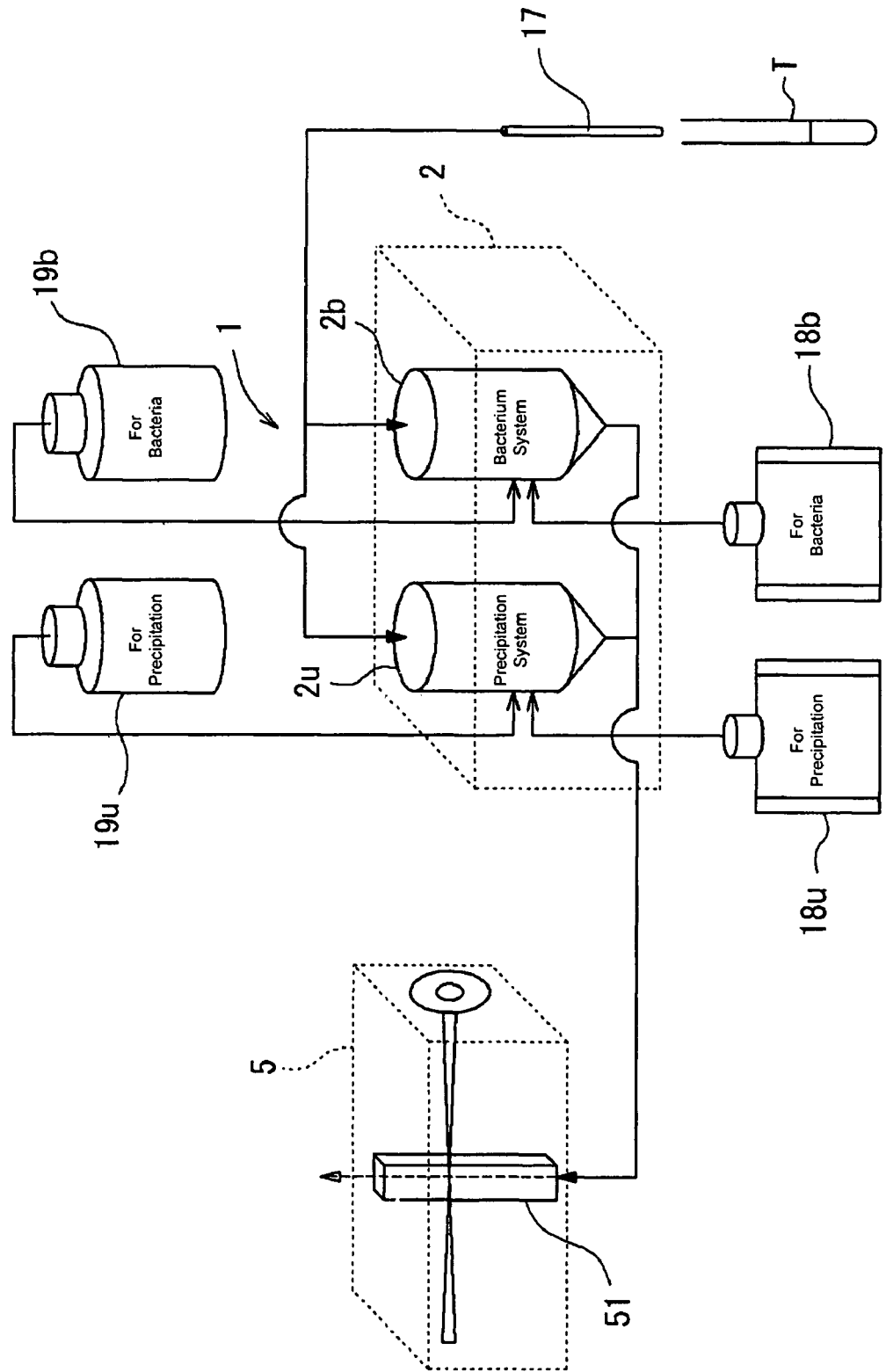
FIG. 3 is a diagram of a schematic function configuration of the sample preparation section and the optical detection section of the urine analysis apparatus.

FIG. 3 is a diagram of a schematic function configuration of the sample preparation section 2 and the optical detection section 5. In the figure, urine (specimen) placed in a test tube T is sucked by a syringe pump (not shown) using a suction tube 17 and is dividedly poured into the sample preparation section by a specimen distribution section 1. The sample preparation section in the embodiment is constituted by a sample preparation section (first sample preparation section) 2u and a sample preparation section (second sample preparation section) 2b; the sample preparation section 2u accommodates an aliquot (first aliquot) of precipitation system for analyzing comparatively large concrete components in urine such as red blood cells, white blood cells, epithelial cells, cylinder, and like; on the other hand, the sample preparation section 2b accommodates an aliquot (second aliquot) of bacterium system for analyzing comparatively small concrete components such as bacteria.

The urine of each of the sample preparation sections 2u, 2b is diluted with a dilution solutions 19u, 19b, respectively, and then stain solutions (stain reagents) 18u, 18b are mixed therewith and the urine specimens are stained by pigments contained in the stain solutions (stain reagents) 18u, 18b, respectively to produce suspensions of concrete components. The sample preparation section 2u prepares a first measurement sample for measuring concrete components in the urine at least containing red blood cells; on the other hand, the sample preparation section 2b prepares a second measurement sample for measuring bacteria.

For two kinds of suspensions (measurement sample) prepared as described above, first, the suspension of the sample preparation section 2u (first measurement sample) is carried to the optical detection section 5, and is surrounded by a sheath solution in a sheath flow cell 51 to form a narrow flow, which is irradiated with a laser beam. Thereafter, in a similar manner, the suspension of the sample preparation section 2b (second measurement sample) is carried to the optical detection section 5, and in a sheath flow cell 51 forms a narrow flow, which is irradiated with a laser beam. This operation is automatically carried out by the control of a microcomputer 11 (control apparatus) as discussed later by operating a drive section, magnetic valve and others (not shown).

Figure 4:
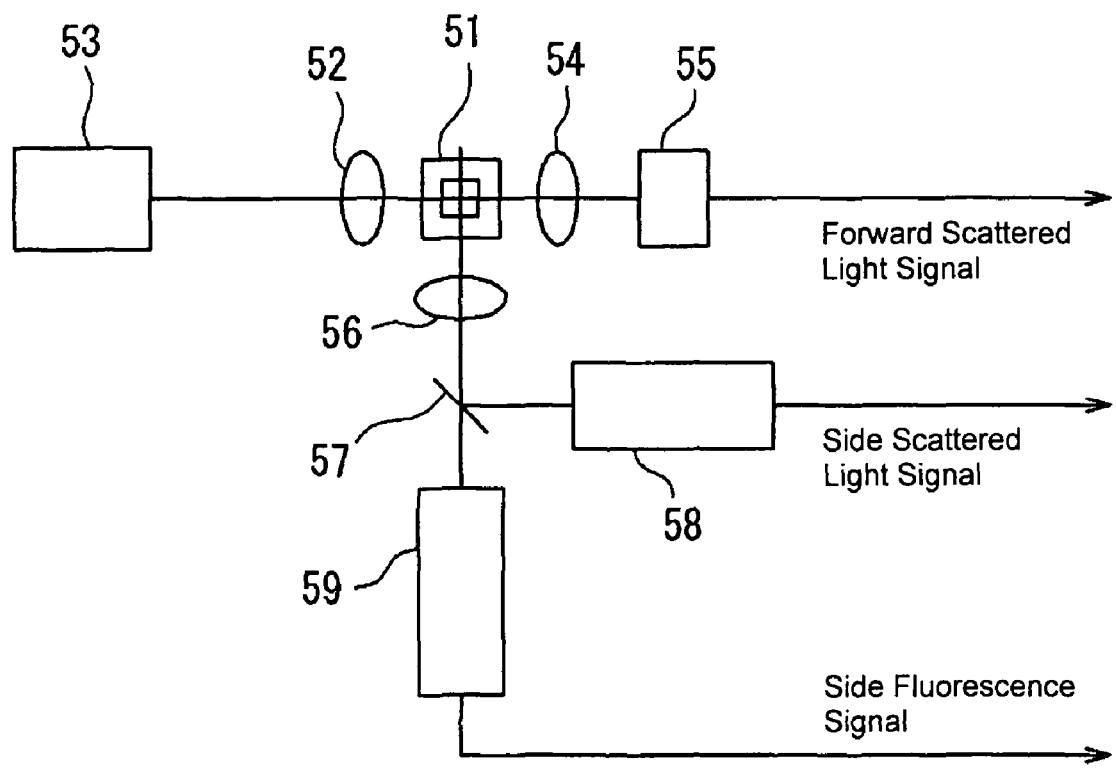
FIG. 4 is a diagram indicating a configuration of the optical detection section.

FIG. 4 is a diagram indicating a configuration of the optical detection section 5. In the figure, a condenser lens 52 condenses a laser beam radiated from a semiconductor laser 53 of being a light source to the sheath flow cell 51; the condensing lens 54 condenses forward scattered light of concrete components in urine to a photodiode 55 that is a scattered light receptive section. Additionally, another condensing lens 56 condenses the side scattered light and side fluorescence of the concrete components to a dichroic mirror 57. The dichroic mirror 57 reflects the side scattered light to a photomultiplier 58 that is a scattered light receptive section, and transmits the side scattered light a photomultiplier 59 that is a fluorescence receptive section. These light signals reflect the characteristics of concrete components in urine. The photodiode 55, photomultiplier 58 and photomultiplier 59 transforms light signals to electric signals and output respectively forward scattered light signals (FSC), side scattered light signals (SSC) and side fluorescence signals (SFL). These outputs are amplified by a pre-amplifier (not shown), and then provided to a next stage processing.

Figure 5:
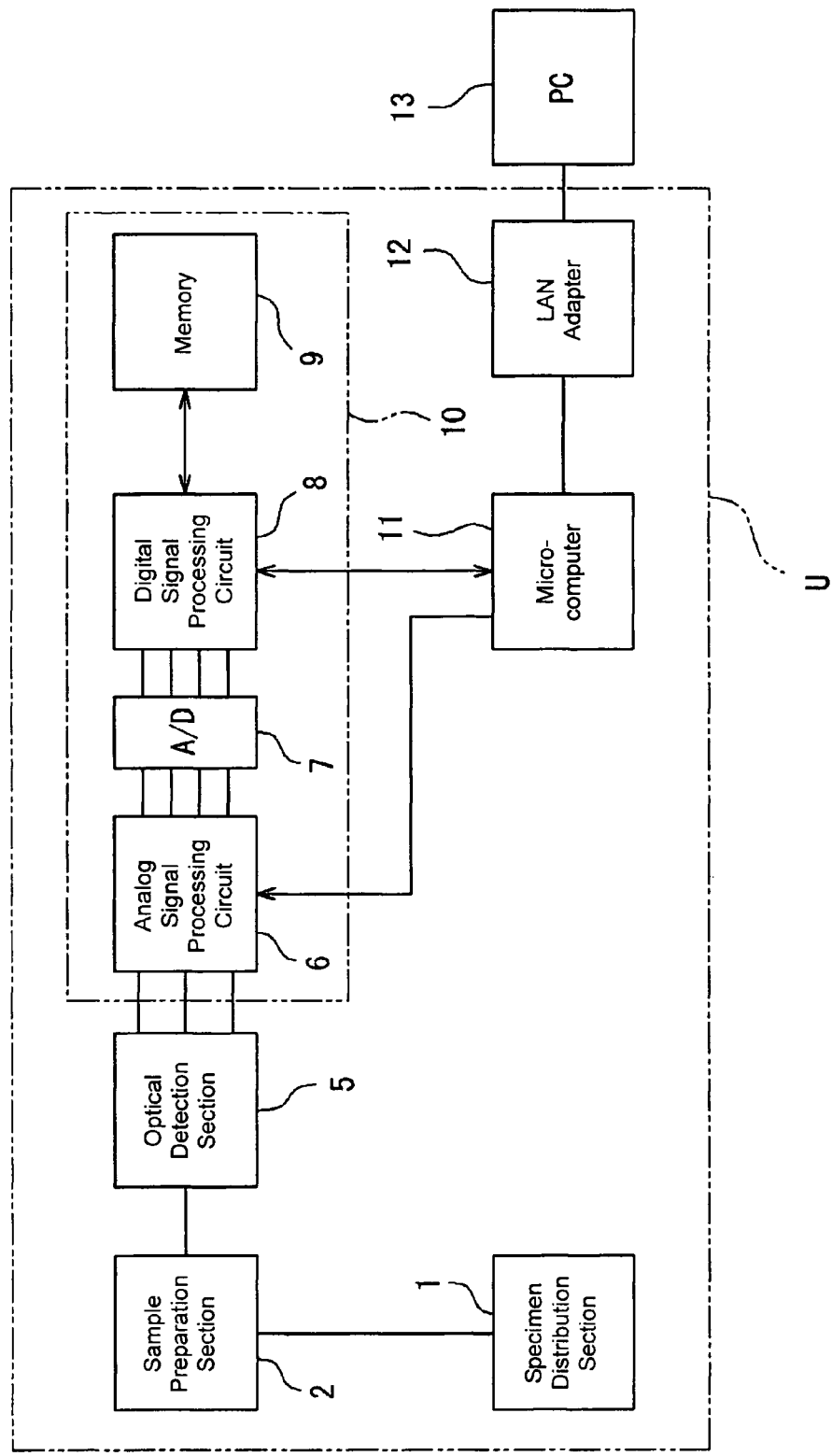
FIG. 5 is a block diagram indicating the whole configuration of the urine analysis apparatus indicated in FIG. 1.

FIG. 5 is a block diagram indicating the whole configuration of the urine analysis apparatus U. In the figure, the urine analysis apparatus U includes the specimen distribution section 1, sample preparation section 2 and optical detection 5 as described above, an analog signal processing circuit 6 of carrying out amplification, filter processing, etc. for the output produced by amplifying the output of the optical detection section 5 by a preamplifier, an A/D converter 7 of transforming the output of the analog signal processing circuit 6 into a digital signal, a digital signal processing circuit 8 of performing a predetermined wave pattern processing for the digital signal, a memory 9 connected to the digital signal processing circuit 8, the microcomputer 11 connected to the analog signal processing circuit 6 and the digital signal processing circuit 8, and a LAN adaptor 12 connected to the microcomputer 11. The outer computer 13 is LAN connected to the urine analysis apparatus U via this LAN adaptor 12; this computer 13 analyzes data obtained in the urine analysis apparatus U. The analog signal processing circuit 6, A/D converter 7, digital signal processing circuit 8 and memory 9 constitute a signal processing circuit 10 for an electric signal the optical detection section 5 outputs.

Figure 6:
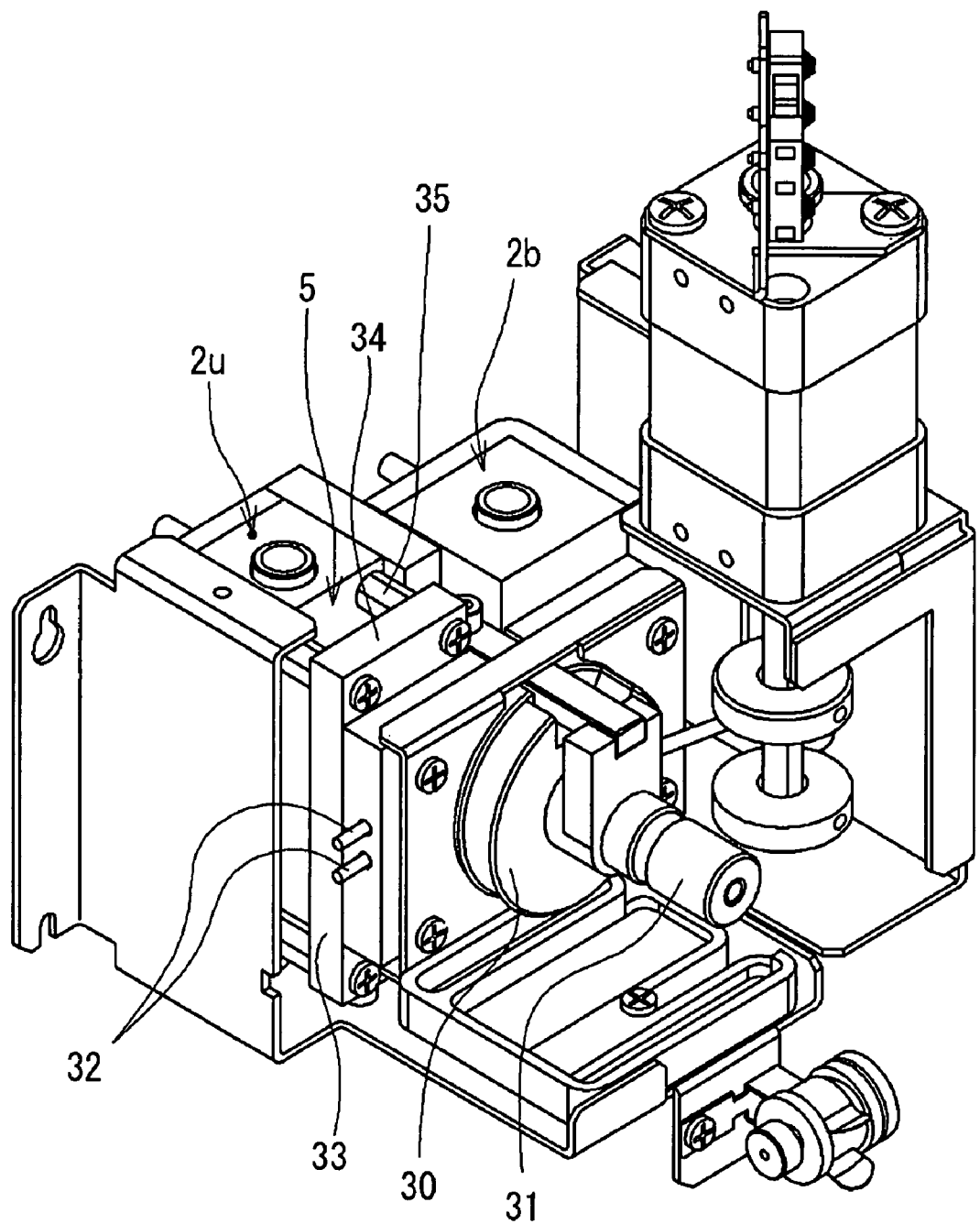
FIG. 6 is a perspective depiction view of the quantitative mechanism and sample preparation section of the urine analysis apparatus.
Figure 7:
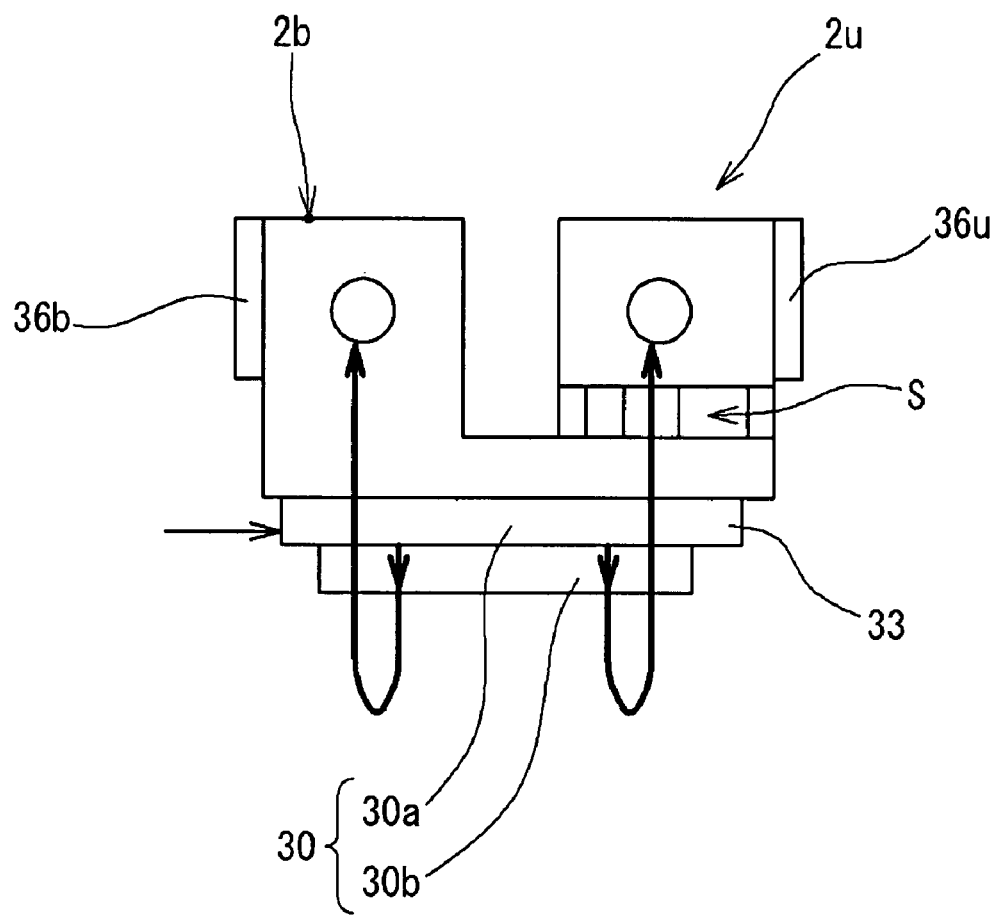
FIG. 7 is a depiction view of the quantitative mechanism and sample preparation section of the urine analysis apparatus.

FIG. 6 is a perspective depiction view of the quantitative mechanism and sample preparation section of the urine analysis apparatus according to the embodiment; FIG. 7 is its depiction view. In the embodiment, a regularly servicing sampling valve 30 is adopted as a quantitative mechanism that distributes a predetermined amount of a urine specimen to the sample preparation section (first sample preparation section) 2u and the sample preparation section (second sample preparation section) 2b. This sampling valve 30 is constituted by two disc-shaped fixed elements and a movable element sandwiched by both the fixed elements; the movable element is rotationally operated by a motor 31.

The above sampling valve 30 includes two alumina ceramic discs 30a, 30b that are overlapped to each other. Inside the discs 30a, 30b a channel for rendering a specimen to flow is formed, and the rotation of the central axis of the disc 30b as the rotational center cuts off the above channel; the discs are integrally constituted by the above sample preparation section 2b via a fluid cassette 33 having therein a channel 32 for specimen. In other words, the sampling valve 30, fluid cassette 33 and sample preparation section 2b are disposed in a closely contacted fashion to each other so as to thermally integrate, and are configured so that the temperature of the sampling valve 30 is made to be substantially equal to the temperature of the sample preparation section 2b. On the contrary, the sample preparation section 2u is fixed to an attaching plate 34 fixed to the basket body by means of a bolt 35 with a specified clearance S, so that the sample preparation section 2u is thermally substantially separated from the above sampling valve 30 and sample preparation section 2b.

The above sample preparation section 2u and sample preparation section 2b are heated respectively by heaters 36u, 36b constituting a temperature regulating section; the temperature of the sample preparation section 2u that prepares the first measurement sample for measuring concrete components in urine containing at least red blood cells is regulated to a first temperature, and also the temperature of the sample preparation section 2b that prepares the second measurement sample for measuring bacteria is regulated to a second temperature higher than the above first temperature. Specifically, the sample preparation section 2u is regulated so as to be about 35±2° C.; the sample preparation section 2b is regulated so as to be 42±2° C. that is higher than the former. As the temperature of a measurement sample is made to be higher, specified sites (membranes or nuclei) of red blood cells, bacteria, and the like contained in the measurement sample can be speedily stained to shorten the measurement time; on the other hand, red blood cells are liable to incur damage at high temperature, so too high a temperature is incapable of precise measurement. Thus, if the temperature of the second measurement sample for measuring high heat resistance bacteria as compared with other concrete components in urine is regulated so as to be higher than the temperature of the first measurement sample for measuring concrete components in urine, that is, if the sample preparation section 2u and sample preparation section 2b each are regulated to a temperature suitable for measurement, concrete components in urine containing red blood cells and bacteria can be both measured with high precision. Additionally, the temperatures of the sample preparation section 2u and sample preparation section 2b can be measured for example by a thermistor. Then, on the basis of these measurement results, on-off control of the above heaters 36u, 36b enables the regulation of the temperatures of the sample preparation section 2u and the sample preparation section 2b to the above specified ranges.

Additionally, configuring so as to thermally integrate the sampling valve 30 and the sample preparation section 2b can prevent cooling of a specimen that is temperature regulated in the sampling valve 30 when the specimen is supplied to the sample preparation section 2b, so the loss of temperature regulation can be reduced. In this case, a sample supplied to the sample preparation section 2u that is kept at a temperature lower than that of the sample preparation section 2b can be naturally decreased in temperature by passing the channel of a specimen through the above clearance S when the sample is supplied from the sampling valve 30.

[Analysis Procedure]

Figure 8:
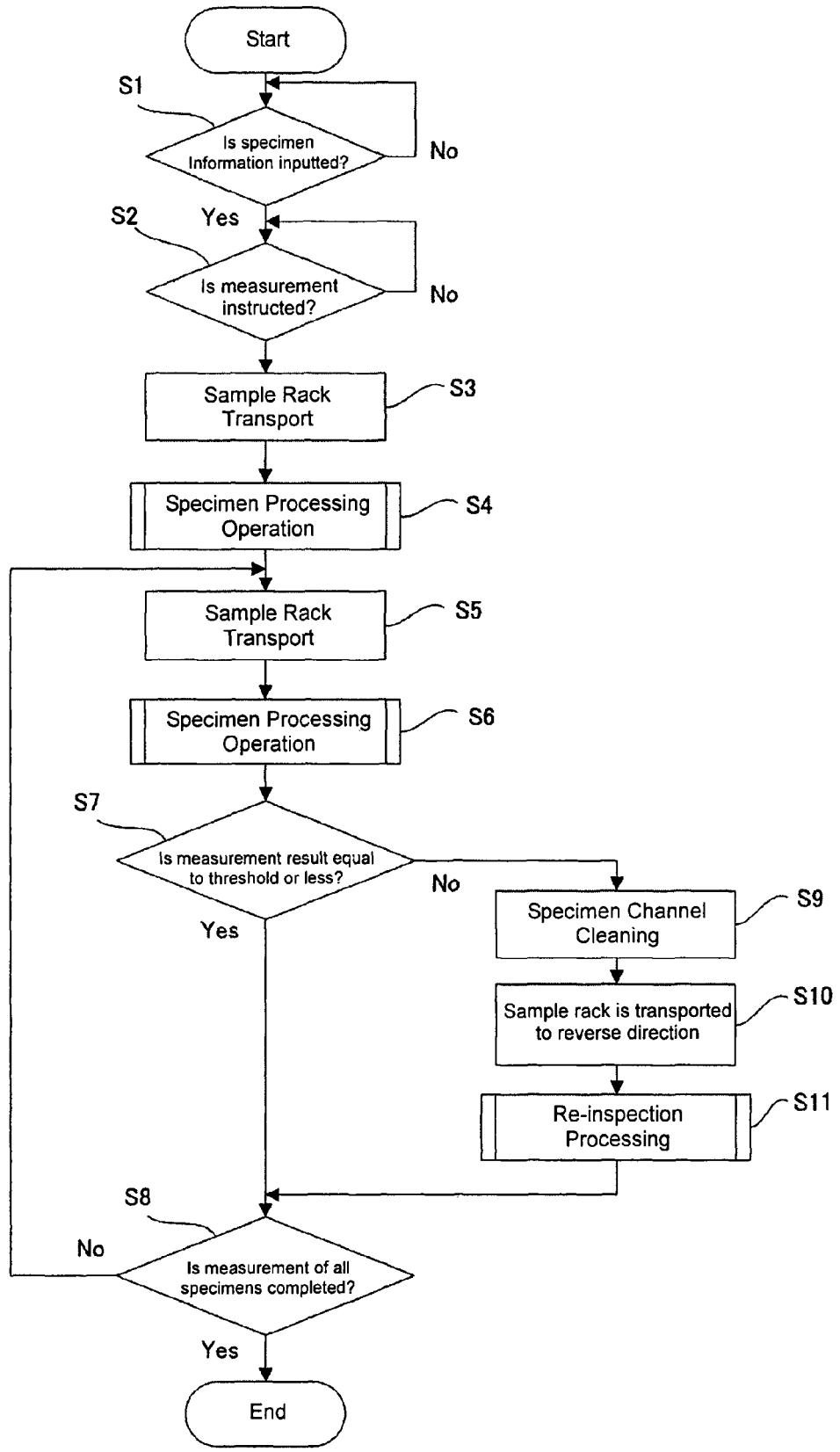
FIG. 8 is a flow chart indicating the analysis procedure of urine using the urine analysis apparatus indicated in FIG. 1.

Next, in accordance with the flow chart indicated in FIG. 8, a procedure of analysis of urine by means of the urine analysis apparatus of the embodiment will be described. First, patient information such as inspection numbers managed by a host computer, and names, ages, sexualities and medical departments related to the inspection numbers, and inspection information such as characteristics to be measured are obtained in advance from the host computer (Step 1). Next, an instruction of measurement execution is done by means of input device (input unit) 13b comprising the key board and mouse of the computer 13 (Step S2). Upon reception of this instruction, a sample rack 3 in which a test tube T containing a specimen is stood is transported to a predetermined sucking position by means of a rack table 4 (Step S3). At this sucking position, the above test tube T is rotated, and the bar code of an ID label is read out that is attached to the periphery of the test tube T. This can inform the specimen number of the specimen, and the characteristics to be measured of the specimen can be specified by collating this specimen number with the specimen information obtained in Step S1.

Figure 9:
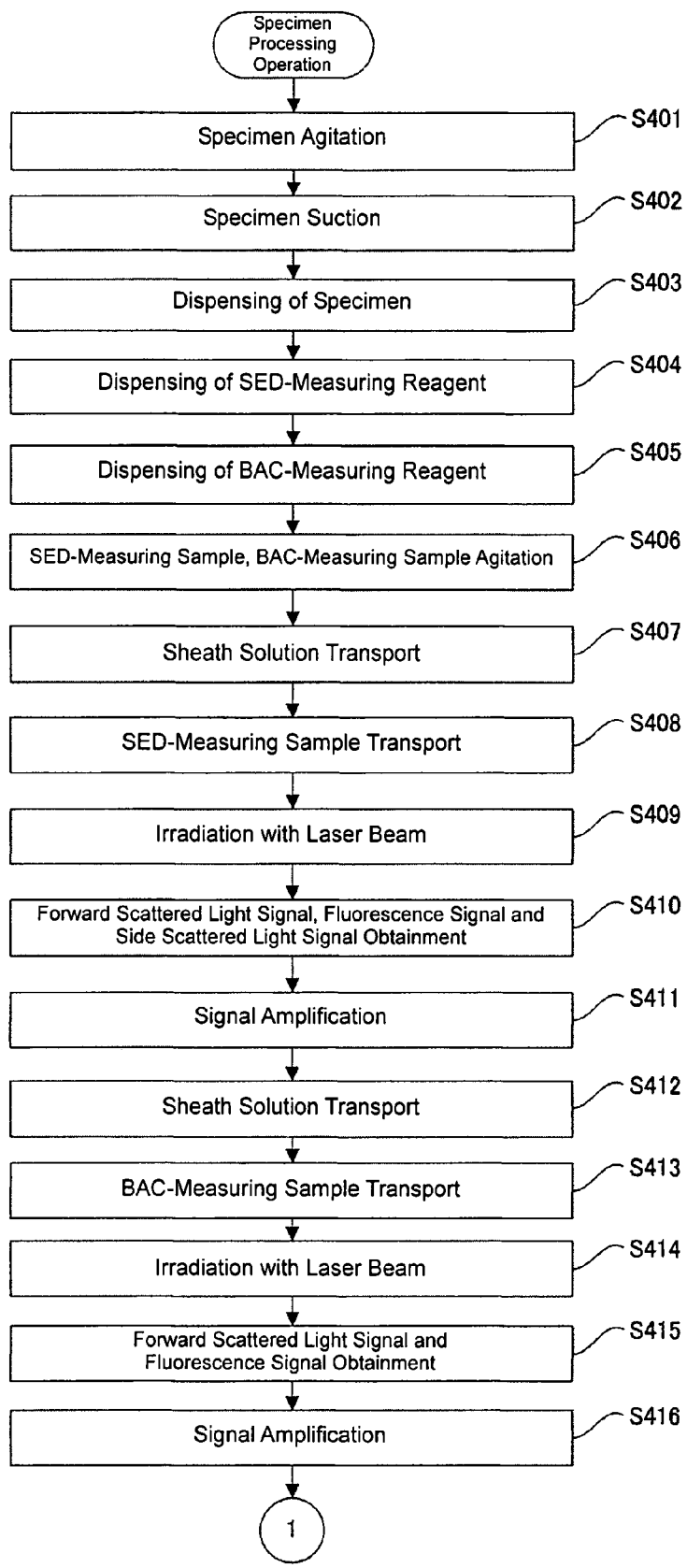
FIG. 9 is a flow chart (first half flow) indicating the procedure of the specimen processing operation indicated in FIG. 8.
Figure 10:
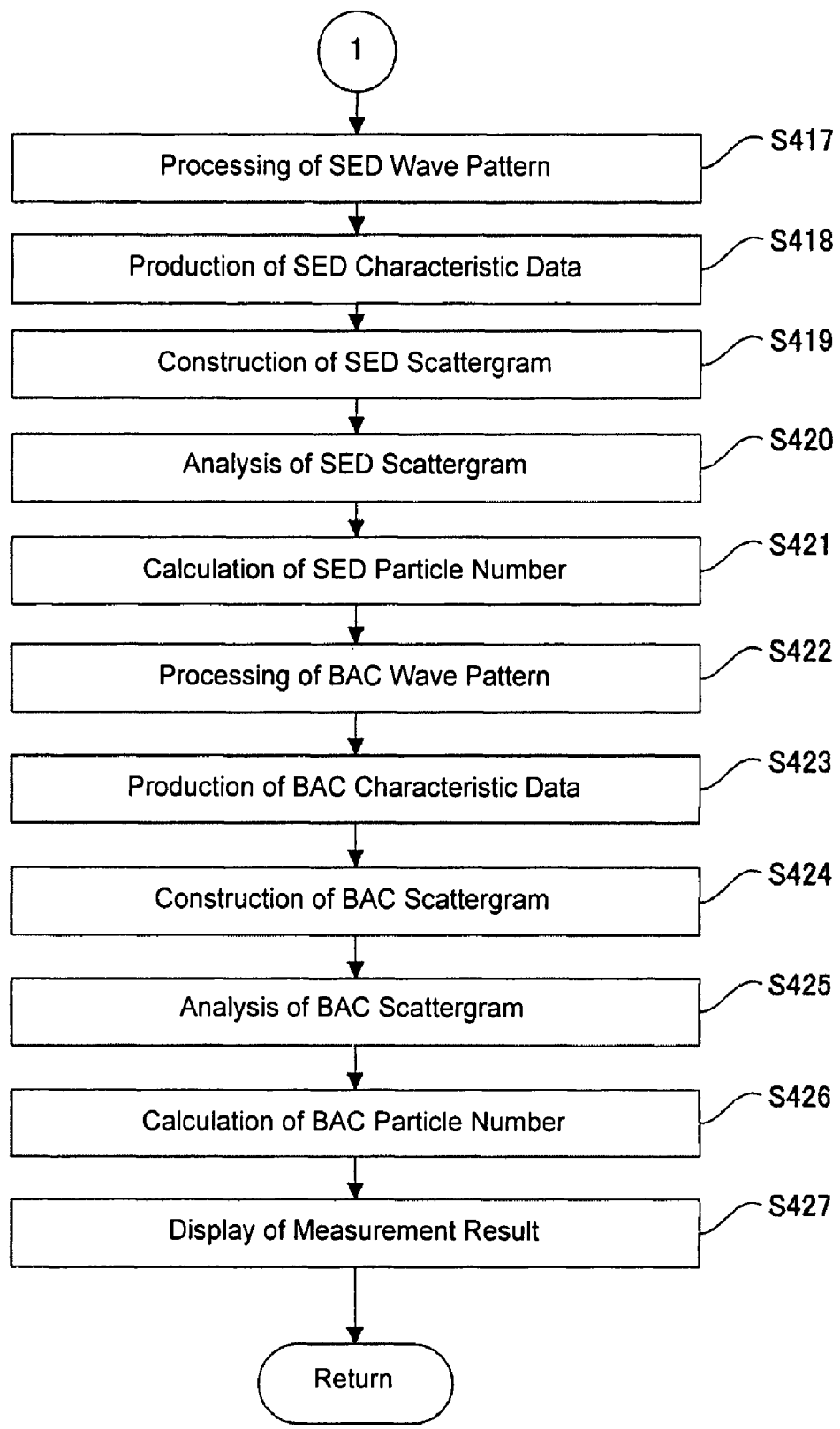
FIG. 10 is a flow chart (latter half flow) indicating the procedure of the specimen processing operation indicated in FIG. 8.

Then, processing of the specimen is carried out (Step S4). In addition, the phase "processing of a specimen" means a series of operations that involves agitating the specimen in a vessel placed at a position for measurement, sucking this specimen to the sample preparation section, mixing the specimen with a reagent in the sample preparation section to prepare a measurement sample, and further carrying out measurement using this measurement sample. FIGS. 9 and 10 show a flow chart indicating an operation procedure of specimen processing. This specimen processing involves, first, descending the suction tube 17 to insert the tip of the suction tube 17 in the specimen within the test tube T, and, while keeping this state, repeating sucking and ejecting the specimen gently to agitate the specimen (Step 401). After agitation, a predetermined amount of the specimen (800 μL) is sucked, and 150 μL and 62.5 μL of the specimens are dividedly poured respectively into the sample preparation section 2u of preparing a measurement sample for measuring concrete components in urine containing at least red blood cells (SED) and the sample preparation section 2b of preparing a measurement sample for measuring bacteria contained in urine (BAC) (Steps S402 and S403).

Into the sample preparation section 2u are dividedly and quantitatively poured the above specimen as well as a predetermined amount of a stain solution (stain reagent) and a dilution solution (Step S404). In a similar manner, into the sample preparation section 2b as well are dividedly and quantitatively poured the above specimen as well as a predetermined amount of a stain solution (stain reagent) and a dilution solution (Step S405). The sample preparation section 2u and sample preparation section 2b are heated respectively with heaters 36u, 36b so as to be predetermined temperatures, and, while keeping this state, the measurement samples are stirred by means of a propeller-shaped stirring tool (not shown) (Step S406). Additionally, the dilution solution dividedly poured into the sample preparation section 2u in Step S405 contains a surfactant, which damages bacterium membranes, thereby being capable of efficiently staining the nuclei of bacteria. Processing of Steps S402 to S405 is actually implemented at the same time.

Then, a sheath solution is delivered to the sheath flow cell 51 of the optical detection section 5 (Step S407), and thereafter, first, the measurement sample for measuring concrete components in urine (SED) is led to the optical detection section 5, and in the above sheath flow cell 51 a narrow flow (sheath flow) enclosed with the sheath solution (Step S408). Subsequently, the sheath flow thus formed is irradiated with a laser beam from the semiconductor laser 53 (Step S409). The reason why the measurement of concrete components in urine is carried out first is that since a surfactant is contained in a sample for bacterium measurement, if the concrete components in urine is measured after measurement of bacteria, in the measurement sample for the concrete components in urine is mingled the surfactant due to carry-over of the measurement sample, so the surfactant incurs damage to the membrane of the concrete components in urine containing red blood cells, thereby affecting influence on the measurement of the concrete component in the urine.

The forward scattered light, fluorescence and side scattered light of the concrete components in the urine, generated by the radiation of the above laser beam, are received respectively by the photodiode 55, photomultiplier 59 and photomultiplier 58 and transformed into electric signals to be thereby outputted as a forward scattered light signal (FSC), fluorescence signal (FL) and side scattered light signal (SSC) (Step S410). These outputs are amplified by a pre-amplifier (Step S411).

When the measurement of the measurement sample for measuring the concrete components in urine (SED) is completed, subsequently, bacteria in the urine are measured using the measurement sample prepared in Step S409. In this case, a forward scattered signal (FSC) and fluorescence signal (FL) are outputted as in Steps 407 to 411 above by means of the optical detection section 5 used in the measurement of the concrete components in the urine, and also amplified (Steps S412 to 416).

The amplified forward scattered light signal (FSC), fluorescence signal (FL) and side scattered light signal (SSC) are transformed into digital signals in the above signal processing circuit 10 (see FIG. 10) and also subjected to predetermined wave pattern processing (Step S417) and then sent to the computer 13 via the LAN adaptor 12. Additionally, in Step S417 the forward scattered light signal (FSC) is amplified in one gain, the fluorescence signal (FL) is amplified in two gains of high and low gains, and the side scattered light signal (SSC) is amplified in one gain.

Then, characteristic data of the concrete component in the urine (SED) (data representing characteristics such as sizes, shapes and inside states of the concrete components in the urine) are produced in the computer 13 (Step S418), and scattergrams are constructed on the basis of these data (Step S419). Thereafter, the clustering of the scattergrams is done by analysis of the scattergrams (Step S420), and the counting of particles for every cluster is performed (Step S421).

As for the bacteria, in a similar manner, the above forward scattered light signal (FSC) and fluorescence signal (FL) amplified are transformed into a digital signal in the above signal processing circuit 10 and also subjected to predetermined wave pattern processing (Step S422). Additionally, in Step S422, the forward scattered light signal (FSC) is amplified in two gains of high and low gains, and the fluorescence signal (FL) is amplified in one gain.

Thereafter, they are sent to the computer 13 via the LAN adapter 12. Then, in the computer 13 characteristic data of the bacteria (BAC) are produced (Step S423), and also a scattergram is constructed on the basis of these data (Step S424). Subsequently, the clustering of the scattergram is done by analysis of the scattergram (Step S425), and the counting of particles for every cluster is performed (Step S426).

Figure 15:
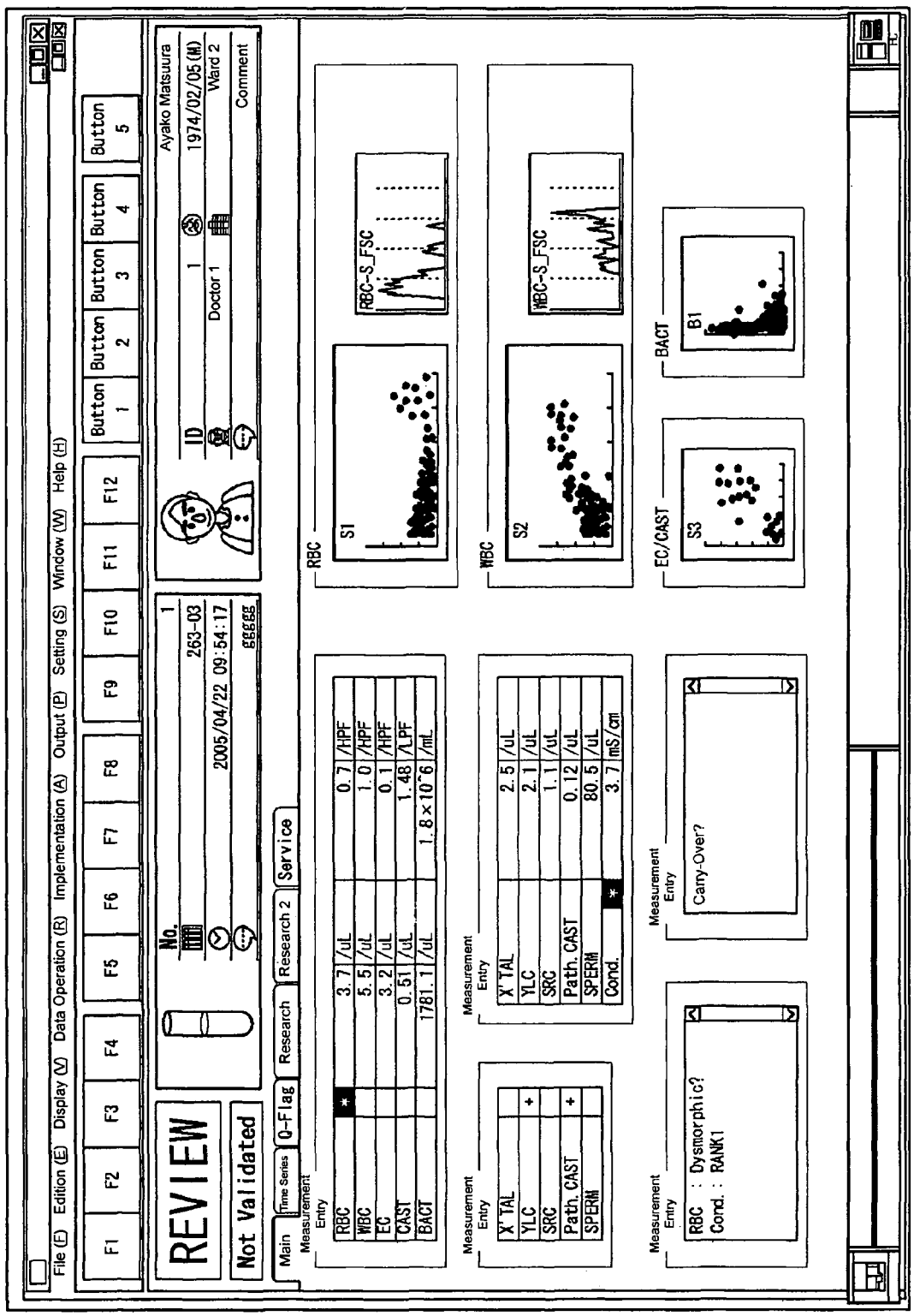
FIG. 15 is a diagram indicating an example of an output screen outputting analysis results.

The measurement results obtained as discussed above are displayed on the display 13a that is the display unit of the computer 13 (Step S427), and the processing is returned. FIG. 15 shows an example of a screen displayed in this manner; the measurement results are displayed by means of numerical values and graphs and also a comment indicating the possibility of occurrence of "carry-over" as described below is displayed.

On the way of the specimen processing operation as discuss above, the sample rack 3 is transported by the rack table 4, the test tube T accommodating a next specimen is positioned in the sucking position (Step S5), and during the execution of processing operation of the former specimen, the processing of the next specimen is initiated (Step S6). In other words, the embodiment is configured so that the specimen processing as described above is continuously carried out on a plurality of urine specimens and, at the time, during the processing operation of a former specimen, the next specimen of the former specimen is initiated. Namely, the embodiment is configured so that a plurality of continuous processing operations are overlapped to each other, so the number of measurement specimens per time can be increased to achieve the speed-up of analysis.

Next, the CPU 104a decides whether or not the result of the preceding measurement, i.e., the result of the bacterium measurement of the specimen examined prior to the specimen that is presently processed is a predetermined threshold or less (Step S7). In Step S7, when the bacterium measurement result is the predetermined threshold or less, whether or not specimens to be measured are all measured is determined (Step S8). Then when the specimens to be measured are all measured, the operation is completed. On the other hand, in Step 8, if specimens to be measured still remain, the processing is returned to Step S5, and the transport of the sample rack (Step S5) and processing of the specimens (Step S6) are carried out. Additionally, in Step S7, if the measurement result exceeds the threshold, cleaning of a specimen passage channel including the sample preparation section and measurement section is carried out (Step S9). Thereafter, the movement of the rack table 4 toward the reverse direction renders the sample rack 3 to be transported to the reverse direction (Step S10), and the processing of the specimen that followed the previous specimen, i.e., the specimen, the measurement result of which is decided to exceed the threshold by Step S7, is initiated again (Step S11). Thereafter, the processing moves to Step S8, where whether or not the specimens to be measured are all measured is determined.

Figure 11:
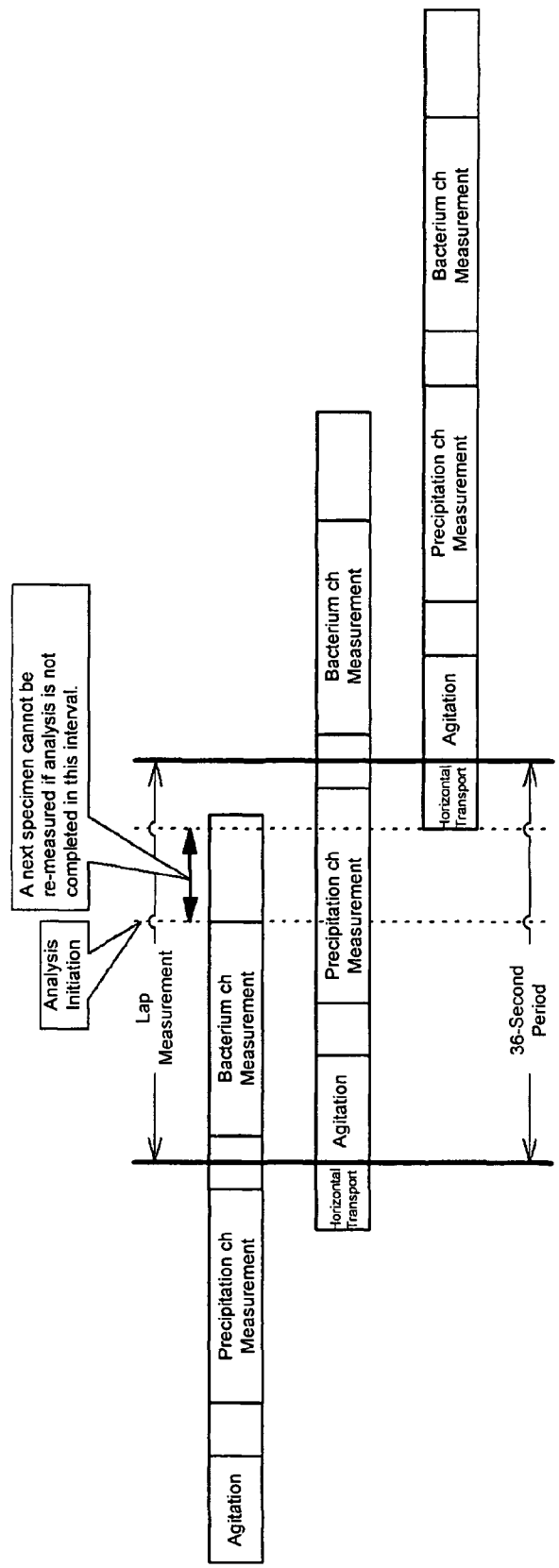
FIG. 11 is a diagram indicating a time chart example of the normal processing operation of a urine analysis apparatus that carries out two kinds of measurements (measurements of concrete components in urine and bacteria).

Overlap operation and re-processing operation of processing of a specimen will be set fort in detail hereinafter. FIG. 11 shows a time chart example of the normal processing operation of the urine analysis apparatus that carries out two kinds of measurements (measurements of concrete components in urine and bacteria). In FIG. 11, the processing operation of three measurement samples is indicated for simplicity. In each processing operation, concrete components in urine such as red blood cells, white blood cells, epithelial cells and cylinder are measured (precipitation channel measurement), and then measurement of bacteria (bacterium channel measurement) is carried out.

First, for a first urine specimen, as discussed above, the tip of the suction tube is inserted in the specimen and, while keeping this state, gentle sucking and ejecting of the specimen is repeated for agitation, the agitated urine specimen is sucked by the suction tube, and further is distributed to a firs sample t preparation section and second sample preparation section by a sampling valve. Then the measurement of concrete components in the urine is carried out using the first measurement sample prepared in this first sample preparation section. Slightly before completion of the measurement of these concrete components in the urine, a test tube containing a second urine specimen is horizontally transported, and is placed in a position where the urine specimen can be sucked by the suction tube. Specifically, a sample rack (test tube stand) is transported by a rack table to place the test tube containing the second urine specimen in place. Additionally, for an increase in specimen processing capacity per time, lap measurement is initiated after completion of horizontal transport of the second urine specimen. In the embodiment, the time interval of measurement is 36 sec.

After the concrete components in the urine for the first urine specimen are measured, bacteria are measured using a second measurement sample prepared in the second sample preparation section. Thereafter, after the completion of measurement of bacteria, the analysis of the measurement results is carried out. This analysis is preferably completed by the initiation of horizontal transport operation of the test tube containing a third urine specimen. In this case, when the concentration of a bacterium in a first urine specimen exceeds a predetermined threshold and this bacterium is in carry-over in a measurement sample prepared from a second urine specimen, a third urine specimen can be prevented from entering a processing mode and remeasurement of the second urine specimen can be smoothly carried out. In other words, if a test tube containing the third urine specimen has been transported to a position sucked by the suction tube, when the second urine specimen is re-inspected, the test tube containing the second urine specimen needs to be returned to the sucking position again after the test tube containing the third urine specimen is moved from the sucking position. Thus, the operation becomes complicated and time loss occurs. However, if the analysis of the measurement result is completed by the initiation of the horizontal operation of the test tube containing the third urine specimen, such complicated operation and time loss can be avoided. Additionally, after completion of the bacterium measurement, the analysis of the measurement result and the usual cleaning of the specimen passage channel are carried out at the same time.

For the second urine specimen also, specimen processing operation is performed in the same procedure as in the first urine specimen. As the result of the above analysis, when the concentration of bacterium in the first urine specimen does not exceed the predetermined threshold, the test tube containing the third urine specimen is horizontally transported slightly before the completion of the measurement of concrete components in the urine of the second urine specimen. Then, on this third urine specimen is carried out specimen processing operation in the same procedure as in the first urine specimen. Thereafter, so long as a bacterium concentration exceeding the predetermined threshold is not detected, the processing operation of fourth and subsequent urine specimens is carried out in the same procedure.

Figure 12:
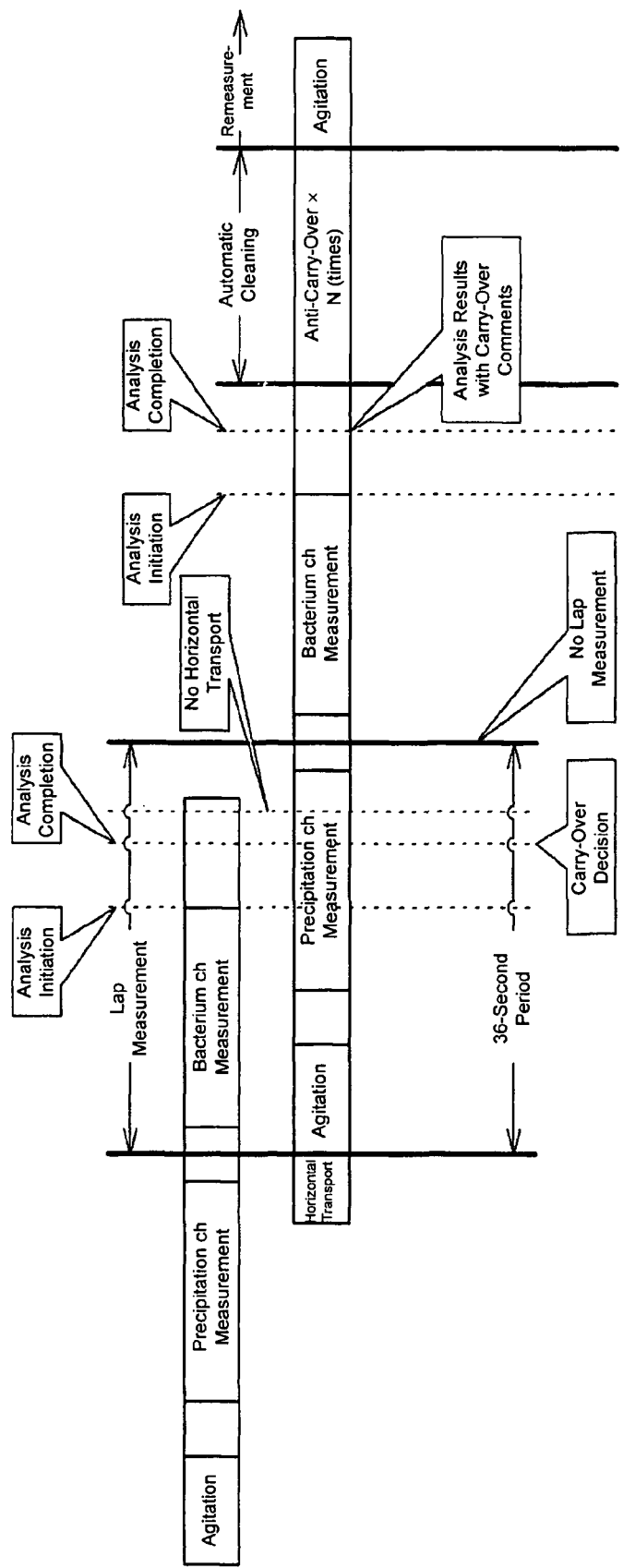
FIG. 12 is a diagram indicating a time chart example of the processing operation of a urine analysis apparatus in the case where there is a urine specimen containing therein a high concentration bacterium.

FIG. 12 shows a time chart example of the specimen processing operation of a urine analysis apparatus in the case where there is a urine specimen containing therein a high concentration bacterium. As a result of the analysis of the measurement result of the first urine specimen, when a bacterium the concentration of which exceeds the predetermined threshold is detected in the urine specimen, a portion of this bacterium group is decided to be carried over in the measurement sample prepared from the second urine specimen, so the test tube containing the third urine specimen is stopped from being horizontally transported. Then, even if the second urine specimen is determined to be carried over, the measurement is carried out in the usual procedure until the bacterium measurement, and the analysis of the measurement result is also preformed. However, the second urine specimen exhibits carry-over of the bacterium from the first urine specimen, so a comment, sign or the like indicating the occurrence of carry-over is attached to the analysis result. This makes it possible for an inspection engineer or the like to decide the measurement result on this second urine specimen to be definitely invalid (not adopted), so that the disadvantage of a large number of particles for a specimen of essentially having a small number of particles being detected can be prevented to thereby guarantee the reliability of the measurement precision.

After completion of processing operation of the second urine specimen, the cleaning of the specimen passage channel including the sample preparation section and measurement section is carried out in order to remove the effect of carry-over caused by the first urine specimen. For this cleaning, basic cleaning operations can be made to be carried out only a predetermined number of times, for example, depending on the concentration of a bacterium in the urine specimen. In this case, only necessary cleaning can be conducted depending on the extent of assumed carry-over, so the cleaning time can be optimized and a reagent and dilution solution used in cleaning can be saved. In addition to being capable of changing the number of times of cleaning, the cleaning time can be altered depending on the bacterium concentration in the urine specimen measured. Further, the concentrations of the above reagent and dilution solution can be also changed depending on the bacterium concentration. These cleaning number of times, cleaning time, and the concentrations of the reagent and dilution solution can also be changed as appropriate in combination. In addition, after measurement of a high value specimen, the same cleaning as the usual one may be made to be performed. In this case also, because the usual cleaning is once carried out prior to the processing of the second urine specimen, consequently two-time cleaning is performed by adding the cleaning prior to the re-processing. Thus, in the re-processing of the second urine specimen, the effect of carry-over comes to be reduced.

After completion of a predetermined cleaning operation, the re-processing of the above second urine specimen is carried out. In this manner, a target specimen of re-processing is re-processed after implementation of cleaning of the specimen passage channel by the cleaning section, so that analysis can be performed on all of the specimens.

Figure 13:
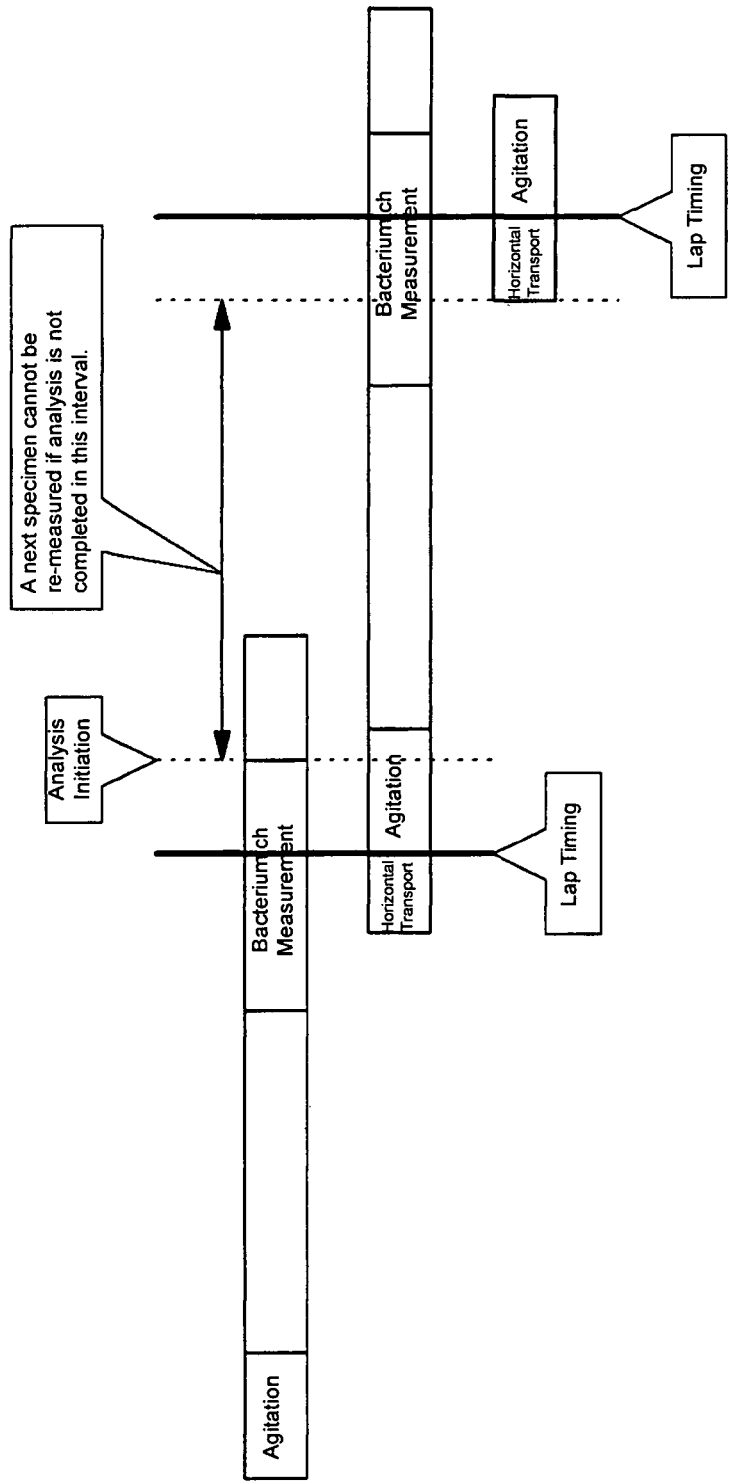
FIG. 13 is a diagram indicating a time chart example of the normal processing operation of a urine analysis apparatus that measures bacteria in urine.

FIG. 13 is a diagram indicating a time chart example of the normal specimen processing operation of a urine analysis apparatus when the urine analysis apparatus measures only bacteria in urine. Such a urine analysis apparatus may also be a urine analysis apparatus for exclusive bacterium measurement, or an apparatus configured such that both modes of measurements of concrete components in urine and bacteria or a mode of measurement of bacteria only can be selected in the urine analysis apparatus depicted in reference with FIGS. 1 to 9.

Also in the example indicating in FIG. 13, the test tube containing the second urine specimen is horizontally transported prior to completion of the processing operation of the first urine specimen, and placed in a position where the urine specimen is sucked by the above suction tube. Then, after completion of bacterium measurement, the measurement result is analyzed. This analysis needs to be completed by the time of initiation of operation of horizontal transport of the test tube containing the third urine specimen as described above.

For the second urine specimen also, specimen processing operation is performed in the same procedure as in the first urine specimen. As the result of the above analysis, when the concentration of bacterium in the first urine specimen does not exceed the predetermined threshold, the test tube containing the third urine specimen is horizontally transported slightly before the completion of the measurement of concrete components in the urine of the second urine specimen. Then, on this third urine specimen is carried out measurement operation in the same procedure as in the first urine specimen. Thereafter, so long as a bacterium concentration exceeding the predetermined threshold is not detected, the processing operation of fourth and subsequent urine specimens is carried out in the same procedure.

Figure 14:
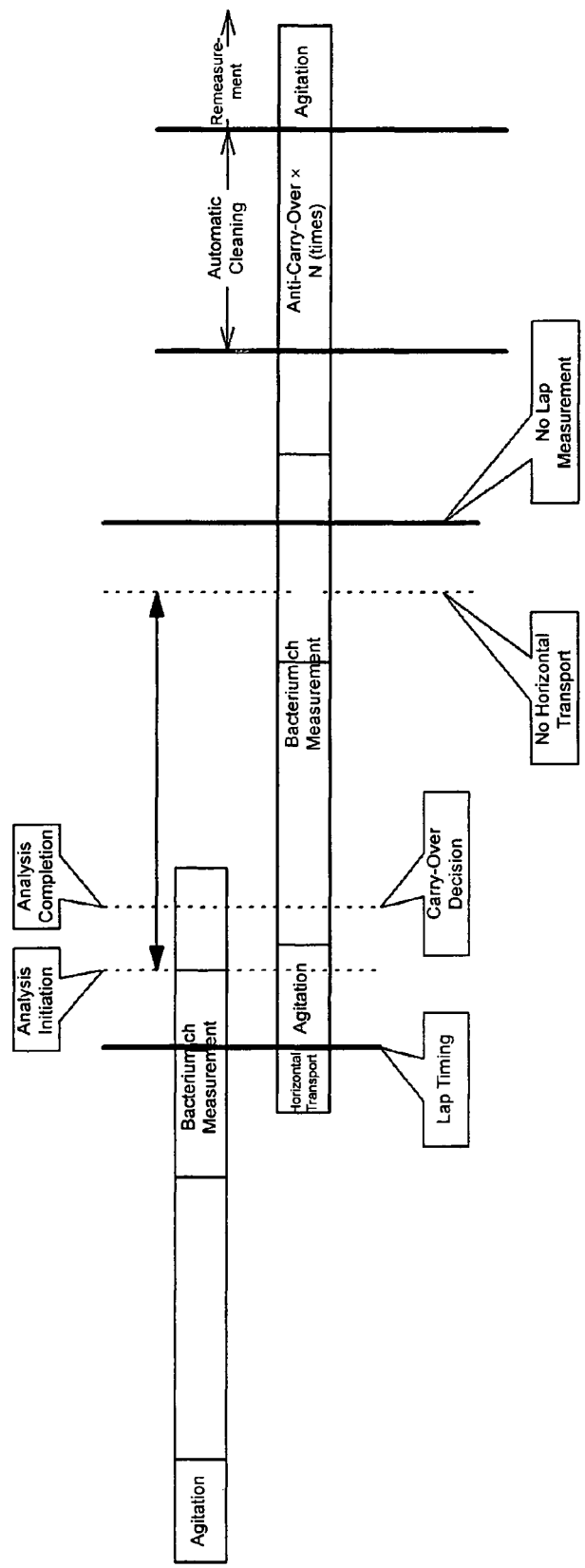
FIG. 14 is a diagram indicating a time chart example of the processing operation of a urine analysis apparatus in the case where there is a urine specimen containing therein a high concentration bacterium.

FIG. 14 shows a time chart example of the specimen processing operation of the urine analysis apparatus in the case where there is a urine specimen containing therein a high concentration bacterium. As a result of the analysis of the measurement result of the first urine specimen, when a bacterium the concentration of which exceeds the predetermined threshold is detected in the urine specimen, a portion of this bacterium group is decided to be carried over in the measurement sample prepared from the second urine specimen, so the test tube containing the third urine specimen is stopped from being horizontally transported. Then, even if the second urine specimen is determined to be carried over, the measurement is carried out in the usual procedure, and the analysis of the measurement result is also preformed. However, the second urine specimen exhibits carry-over due to the bacterium in the first urine specimen, so a comment, sign or the like indicating the occurrence of carry-over is attached to the analysis result. This makes it possible for an inspection engineer or the like to decide the measurement result on this second wine specimen to have an effect of the carry-over.

After completion of processing operation of the second urine specimen, the cleaning of the specimen passage channel including the sample preparation section and measurement section is carried out in order to remove the effect of carry-over caused by the first urine specimen. The description of this cleaning is as in the example indicated in FIGS. 11 and 12, and thus is omitted. Thereafter, after completion of the predetermined cleaning operation, the remeasurement of the above second urine specimen is carried out.

In the embodiment as discussed above, as a result of analysis of the measurement result of the previous specimen, when a particle concentration that exceeds a predetermined threshold is detected, the cleaning of the specimen passage channel including the sample preparation section and measurement section is carried out and also the re-processing of the next specimen is performed after cleaning, after completion of the processing operation of the next specimen. However, without performing such cleaning and re-processing, the need for remeasurement may be indicated in the measurement result of the above next specimen by means of an appropriate sign or comment.

In other words, the embodiment is configured so that the processing operation of the next specimen of a previous specimen is initiated during the processing operation of the pervious specimen, and also as a result of the particle measurement of a previous specimen, when the particle concentration in the previous specimen exceeds the threshold, the embodiment is also configured so that the need for remeasurement is indicated in the result of the particle measurement of the next specimen.

This embodiment is also configured so that the processing operation of the next specimen of a previous specimen is initiated during the processing operation of the pervious specimen and that a plurality of continuous processing operation are overlapped to each other, so the number of processing specimens per time is increased to be capable of achieving the speed-up of the analysis. On the other hand, when the particle concentration in a measurement sample exceeds the threshold, in the measurement sample to be measured next to this specimen, particles in the previous specimen are thought to be carried over in large numbers. Hence, for the next specimen, although the processing operation is executed in accordance with a predetermined procedure, to the result of particle measurement obtained is attached a comment such as "carry-over/remeasurement". This renders it possible to inform a user that the above next specimen is a specimen needed to be re-measured and for the user to take appropriate measures such as executing remeasurement for the specimen even in the case where high value is measured for the specimen that in fact has small number of particles due to the effect of carry-over. Execution of remeasurement for such a specimen is capable of achieving speed-up of the analysis while avoiding the effect of carry-over and guaranteeing the reliability of measurement precision.

The specimen transport section is preferably configured so as to not only proceed but be capable of retreating, which enables the return of the above specimen to a position for measurement by operation and time as little as possible, even in the case where a specimen is re-measured that is made to once proceed from a measurement position on the sequence.

Figure 16:
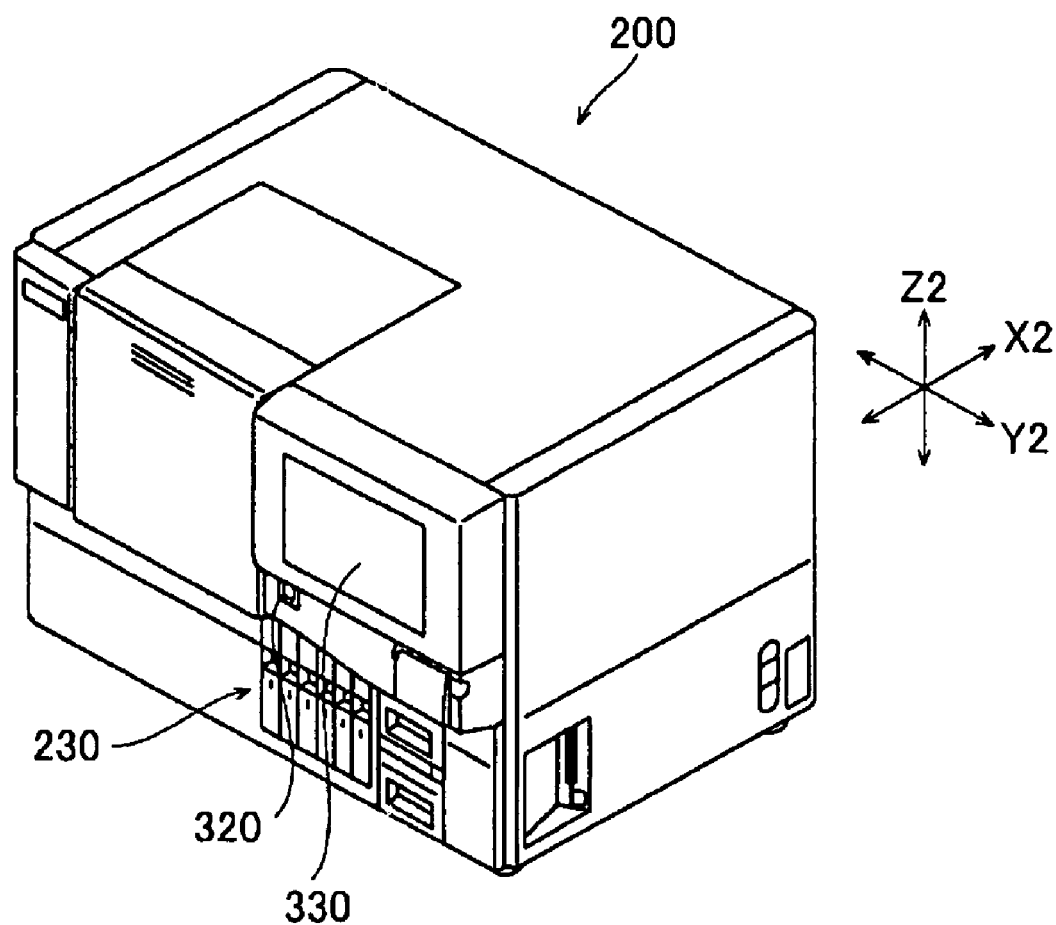
FIG. 16 is a perspective view indicating the whole construction of an immune aggregation measurement apparatus according to another embodiment of the present invention.
Figure 17:
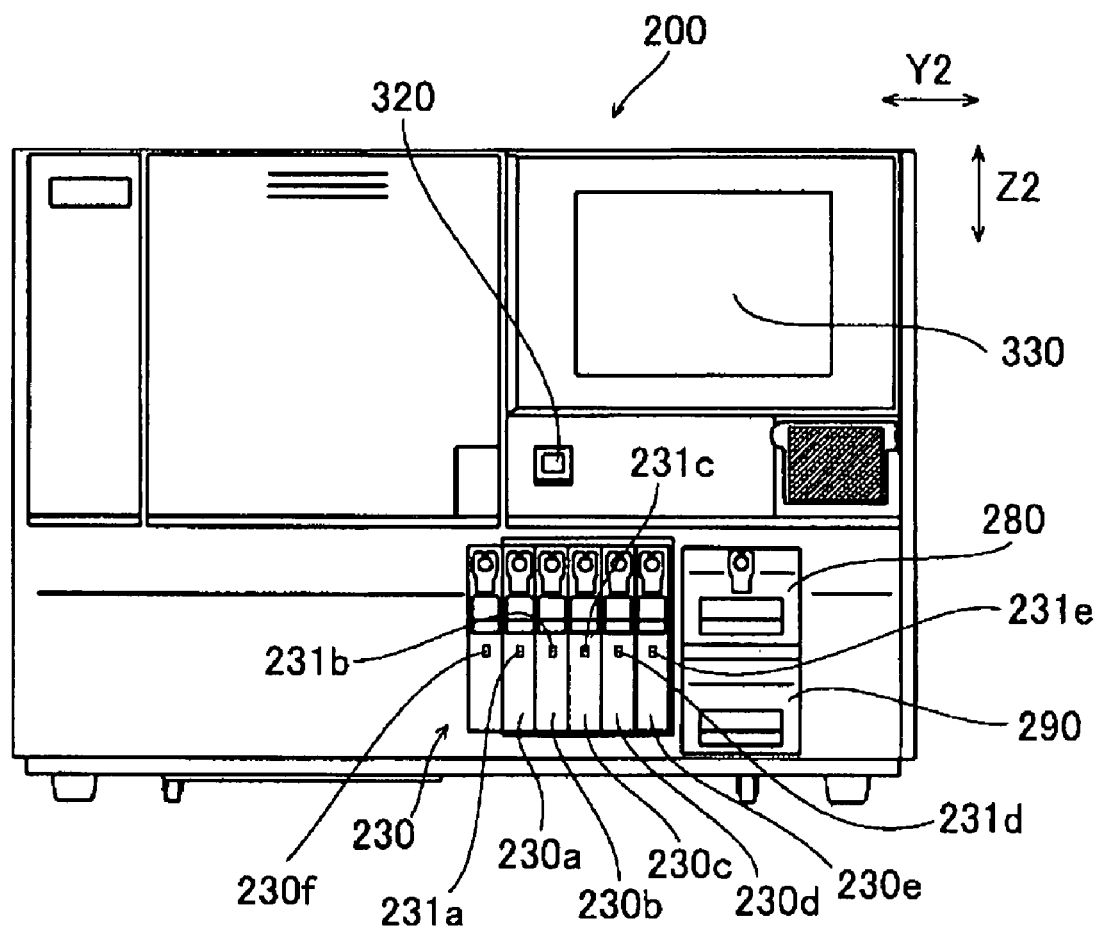
FIG. 17 is a front view of the immune aggregation measurement apparatus according to the embodiment indicated in FIG. 16.
Figure 18:
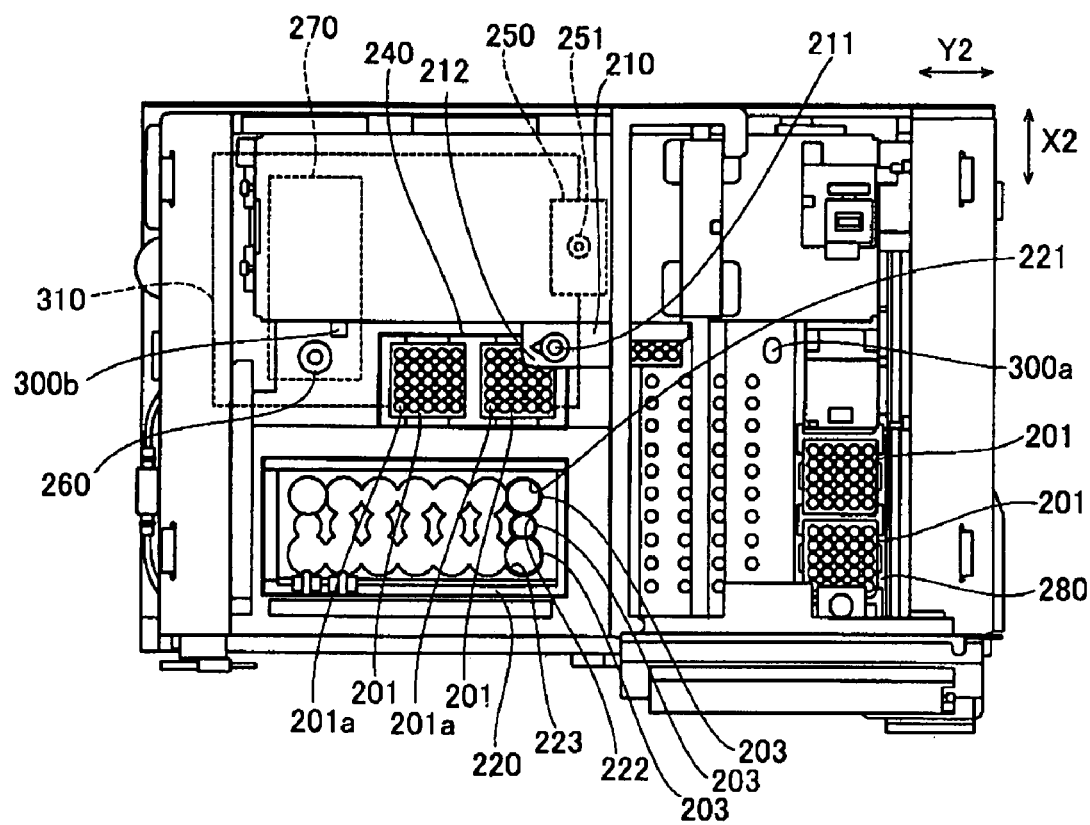
FIG. 18 is a plan view indicating the inner configuration of the immune aggregation measurement apparatus according to the embodiment indicated in FIG. 16.

Next, another embodiment of a specimen analysis apparatus of the present invention will be set forth. An immune aggregation measurement apparatus 200 according to the other embodiment of the present invention includes, as shown in FIGS. 16 to 18, a dispensing section 210, reagent placement section 220, specimen holder section 230, reaction section 240, measurement dilution dispensing section 250, sample receptive section 260, optical detection section 270, reaction plate tray 280 accommodating an unused reaction plate 201, reaction plate disposal box 290 storing a used reaction plate 201, cleaning sections 300a and 300b, and control section 310. As shown in FIGS. 16 and 17, the front face of the immune aggregation measurement apparatus 200 has disposed thereon an electric source switch 320 for starting the apparatus and a display section 330 comprised of a touch panel.

The dispensing section 210 is configured so as to move between a rack 231 of specimen holders 230a to 230e as discussed later and the reaction section 240. This dispensing section 210 includes, as shown in FIG. 18, a horizontal direction movement mechanism section (not shown) that is movable to both the X2 axis direction running perpendicular to the horizontal direction and the Y2 axis direction, a specimen and latex pipette section 211 that is movable to the direction (Z2 axis direction) running perpendicular to the horizontal direction movement mechanism section, and a plate catcher section 212. Additionally, the specimen and latex pipette section 211 has a mechanism that dividedly pours and ejects a sample (whole blood and serum) within a sample cup 202 (see FIG. 19) mounted on the rack 231 of the specimen holders 230a to 230e as described below. The specimen and latex pipette section 211 has a mechanism that dividedly pours and ejects a latex reagent, buffer and specimen dilution solution within a reagent bottle 203 set to a reagent placement section 220 as discussed later. The plate catcher section 212 is provided for transporting the unused reaction plate 201 from the reaction plate tray 280 to the reaction section 240 as well as transporting the used reaction plate 201 to the reaction plate disposal box 290. The reaction plate 201 is equipped with 25 cuvettes 201a that are capable of accommodating samples and various reagents.

The reagent placement section 220 is provided for mounting the reagent bottle 203 that has accommodated a buffer, latex reagent and specimen dilution solution. Now, reagents (buffer, latex reagent, specimen dilution solution) within a reagent bottle 203 are kept at a predetermined temperature (15° C. or less). The reagent placement section 220 is provided with, in order from the inner part, a buffer vessel set section 221, latex reagent vessel set section 222, and specimen dilution solution vessel set section 223. These three reagents (buffer, latex reagent, specimen dilution solution) are set for every characteristic to be measured; the reagent set section is configured so as to be capable of measuring seven kinds of characteristics.

Figure 19:
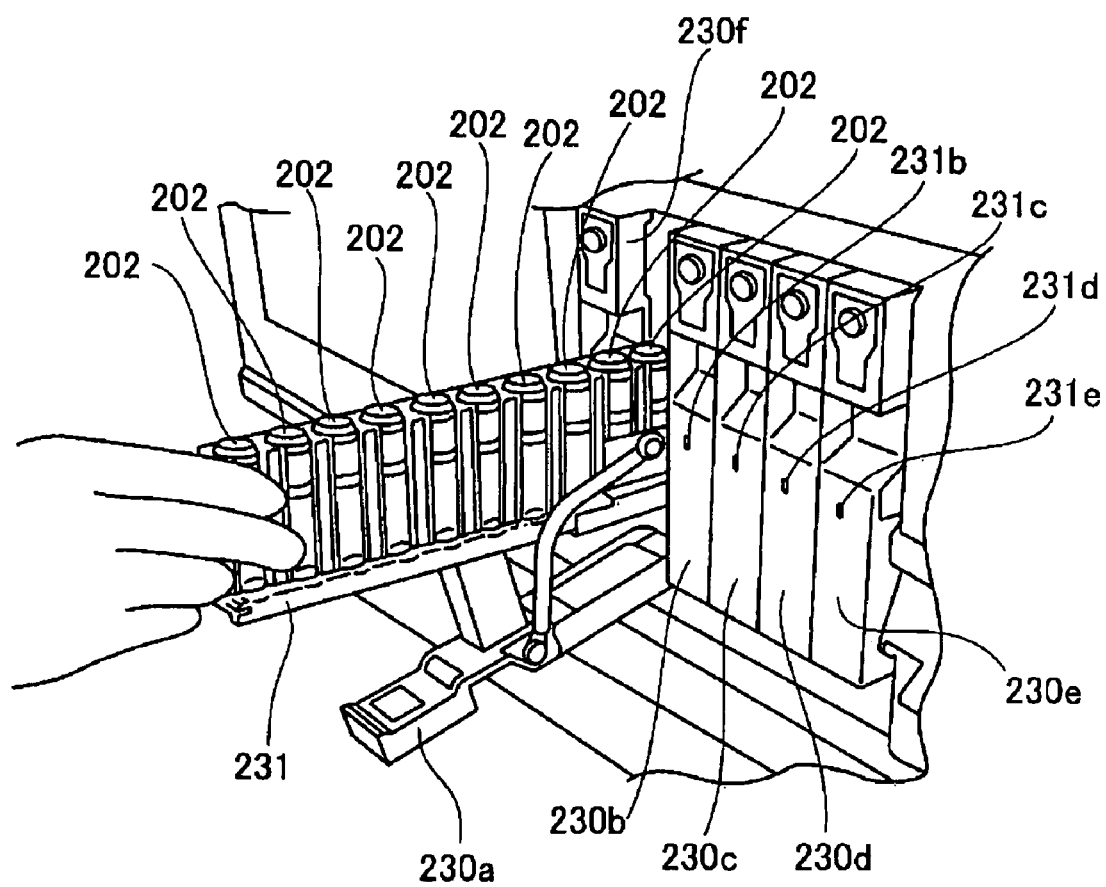
FIG. 19 is an enlarged perspective view of the specimen holder section of the immune aggregation measurement apparatus according to the embodiment indicated in FIG. 16.

The specimen holder section 230 is provided for processing all samples with order registration in the order predetermined. This specimen holder section 230 comprises, as indicated in FIG. 19, five specimen holders 230a to 230e for setting the rack 231 capable of mounting 10 sample cups 202 and one emergency specimen holder 230f for setting the rack 231 capable of mounting one sample cup 202. The rack 231 of the specimen holders 230a to 230e can mount 10 sample cups 202; to the five specimen holders 230a to 230e can totally set 50 sample cups 202. The racks 231 of the specimen holders 230a to 230e is disposed, in the order from left as viewed from the front of the apparatus, respectively in a rack set position 1, a rack set position 2, in a rack set position 3, in a rack set position 4, and in a rack set position 5. Sample cups 202 mounted on racks 231 of the five specimen holders 230a to 230e are disposed, in order from the inner part of the apparatus, respectively in cup set position 1 to cup set position 10.

In predetermined positions of the racks 231 of the specimen holders 230a to 230e of the specimen holder section 230 are mounted one sample cup 202 accommodating a precision control sample. In the front faces of the five specimen holders 230a to 230e of the specimen holder section 230 are placed respectively specimen LEDs 231a to 231e (see FIGS. 17 and 19). In the front faces of the emergency specimen holder 230f as well, an emergency specimen LED 231f (see FIG. 17) is placed. These specimen LEDs 231a to 231e and the emergency specimen LED 231f are configured so as to be lighted in green when the specimen holders 230a to 230e and the emergency specimen holder 230f is capable of being pulled out, and lighted in red when they are incapable of being pulled out. A user can add the sample cup 202 to the racks 231 of the specimen holders 230a to 230e and the emergency specimen holder 230f when the specimen LEDs 231a to 231e and the emergency specimen LED 231f are lighted in green.

An emergency specimen sample within the sample cup 202 held on the rack 231 set in the emergency specimen holder 230f intrudes into a sample within the sample cup 202 held in the rack 231 set in the specimen holders 230a to 230e and is measured preferentially.

Figure 20:
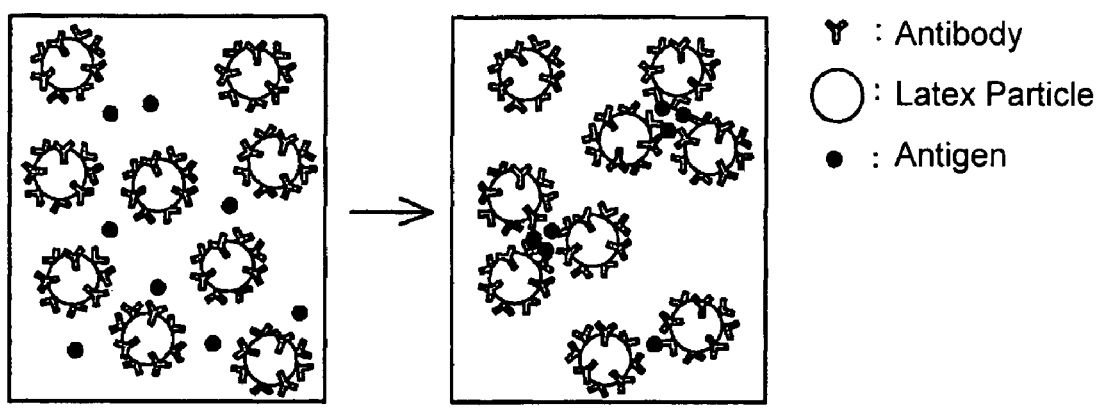
FIG. 20 is a diagram indicating an aggregation reaction of antibodies bonding to antigens and latex particles.

The reaction section 240 is placed in order that a sample and emergency specimen sample accommodated within the cuvette 201a of two sheets of reaction plates 201 are allowed to react with various reagents (buffer, latex reagent, specimen dilution solution). Specifically, the reaction section involves agitating samples dividedly poured by the dispensing section 210 as described above and an emergency specimen sample and various reagents (buffer, latex reagent, specimen dilution solution) and mixing them, maintaining the agitated and mixed samples and emergency specimen sample and various reagents at a predetermined temperature to prepare a preparation sample, and promoting the aggregation reaction of the latex reagent. In other words, in this reaction section 240, as shown in FIG. 20, an aggregation reaction is carried out in which latex particles within a latex reagent to which an antibody is bonded are aggregated by way of an antigen within a sample.

The measurement dilution dispensing section 250 is disposed behind the dispensing section 210, as shown in FIG. 18, and has a function of sucking and ejecting a preparation sample within the cuvette 201a of the reaction plate 201 of the reaction section 240. This measurement dilution dispensing section 250 includes a horizontal direction movement mechanism section (not shown) that is movable to the X2 axis direction running perpendicular to the horizontal direction and the Y2 axis direction, and a measurement dilution pipette section 251 that is movable to the direction (Z2 axis direction) running perpendicular to the horizontal direction movement mechanism section. The measurement dilution dispensing section 250 ejects a sucked preparation sample within the cuvette 201a of the reaction plate 201 together with a measurement dilution solution accommodated in a tank (not shown) disposed below the immune aggregation measurement apparatus 200 to the sample receptive section 260.

The sample receptive section 260 is placed in order to receive a preparation sample and measurement dilution solution within the cuvette 201a of the reaction plate 201 of the reaction section 240 as discussed above. A particle suspension solution (preparation sample and measurement dilution solution) received to the sample receptive section 260 is guided to a sheath flow cell 274 (see FIG. 21) of the optical detection section 270 as discussed later.

Figure 21:
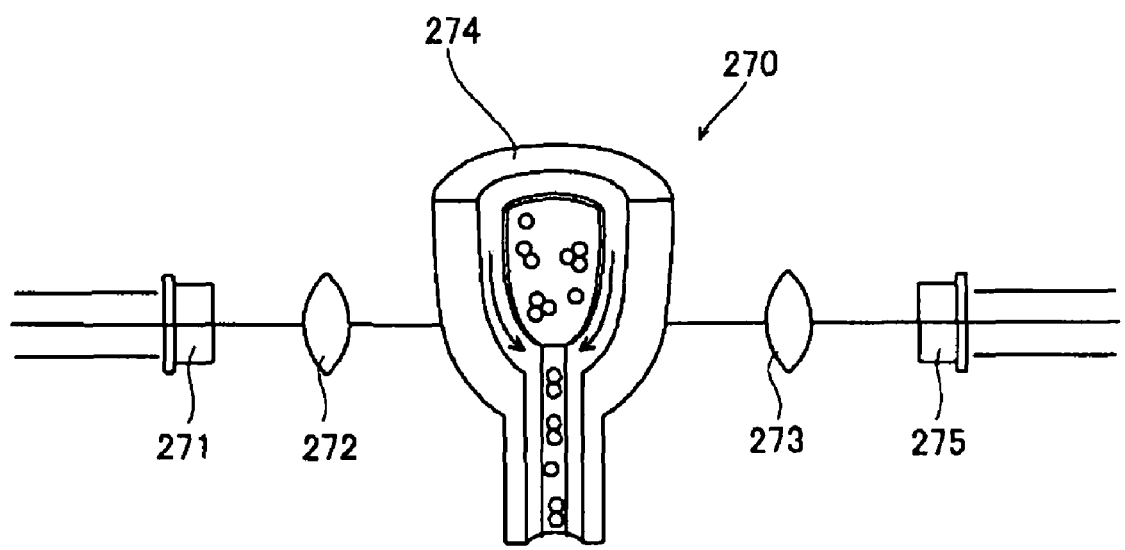
FIG. 21 is a scheme of the optical detection section of the immune aggregation measurement apparatus according to the embodiment indicated in FIG. 16.

The optical detection section 270 comprises, as shown in FIG. 21, a laser diode 271 as a light source, a condenser lens 272 and collector lens 273, the sheath flow cell 274, and a photodiode 275 as a light receptive element. The sheath flow cell 274 has a function of converting the flow of the particle suspension solution (preparation sample and measurement dilution solution) to a flat flow by sandwiching the sheath flows that flow through both sides of the particle suspension solution. Additionally, the sheath flow cell is configured so that the light with which the particle suspension solution flowing through the sheath flow cell 274 from the laser diode 271 is irradiated is reflected by aggregated lumps of latex particles in the particle suspension solution (see FIG. 20) and received by the photodiode 275.

The reaction plate tray 280 can accommodate at the maximum four unused reaction plates 201 (see FIG. 18), as shown in FIGS. 16 and 17. The reaction plate 201 accommodated in the reaction plate tray 280 is transported to the reaction section 240 by means of the plate catcher section 212 of the dispensing section 210 (see FIG. 18). The reaction plate disposal box 290 can store the used reaction plate 201, which is transported from the reaction section 240 by the plate catcher of the dispensing section 210.

The cleaning section 300a is disposed for cleaning the dispensing section 210 and specimen and latex pipette section 211. The cleaning section 300b is provided for cleaning the measurement dilution pipette section 251 of the measurement dilution dispensing section 250.

Next, the screen layout of the display 330 will be set forth in detail in reference with FIGS. 16 and 17 and 19 to 25. The display 330 (see FIG. 16) is disposed for displaying a screen (progress state screen) displaying the measurement results (concentrations, graphs, and others) calculated from the intensity of the scattered light received by the optical detection section 270 (see FIG. 21) (see FIGS. 23 and 24), a screen (measurement registration screen, see FIG. 22) carrying out measurement instructions (order registration) such as sample IDs of samples and precision control samples, and others.

Figure 22:
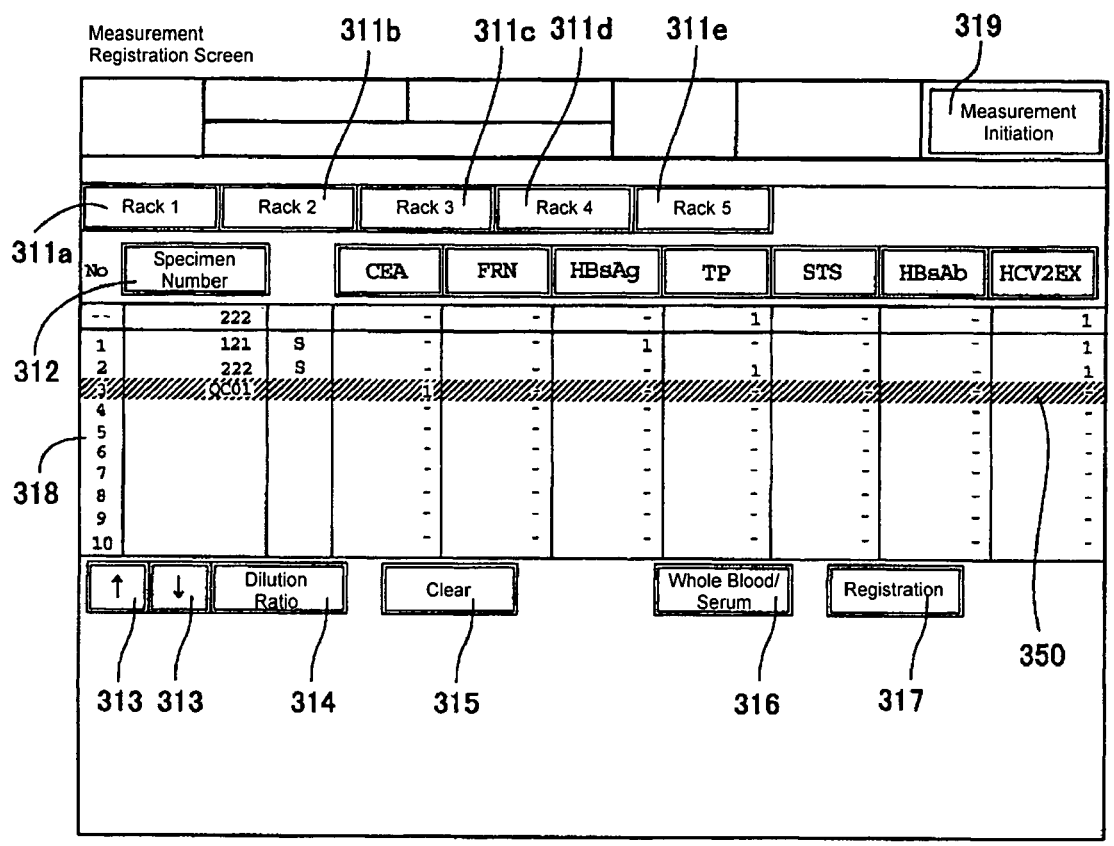
FIG. 22 is a diagram indicating a measurement registration screen displayed on a display section of the immune aggregation measurement apparatus according to the embodiment indicated in FIG. 16.

On the measurement registration screen are displayed, as illustrated in FIG. 22, five rack designation buttons 331a to 331e designating the racks 231 of the specimen holders 230a to 230e, a specimen number input button 312 used when a specimen number is registered, cursor movement buttons 313 used when a cursor 350 is moved, a dilution ratio input button 314 used when a dilution ratio is registered, a clear key 315 for erasing the specimen number and dilution ratio inputted, a whole blood/serum input button 316 for designating the kind of a sample (whole blood or serum), a registration button 317 of settling the sample order-registered as a measurement (dispensing) target, an order list display section 318 of displaying the content of order registration, and a measurement initiation button 319.

Five rack designation buttons 311a to 311e are disposed for designating the rack 231 of predetermined specimen holders 230a to 230e of the specimen holder section 230. For example, if a user touches the rack designation button 311a ("rack 1" in the screen), a rack 231 (see FIG. 19) mounted on the specimen holder 230a of the specimen holder section 230 is designated, thereby enabling the order registration of a rack 231 mounted on the specimen holder 230a. Additionally, the specimen number input button 312 is used when samples of the cup set positions 1 to 10 selected by the cursor 350 moved by touching the cursor movement button 313 and sample IDs of precision control samples are inputted. For this sample ID, in addition to IDs corresponding to samples, an ID corresponding to the precision control sample is inputted. As sample IDs, for example, "121 and 222" are used. As a sample ID of the precision control sample, for example, "QC01" is used. For example, when the precision control sample is accommodated in the sample cup 202 corresponding to the cup set position 3 of the rack set position 1, a user touches the rack designation button 311a to display the content of the order registration of the rack set position 1 on the order list display section 318. Thereafter, the cursor 350 is positioned at the cup set position 3 using the cursor movement button 313, and registered as "QC01" using the specimen number input button 312.

The dilution ratio input button 314 is used when the dilution ratios of the samples of the cup set positions 1 to 10 selected by the cursor 350 are inputted. Additionally, the whole blood/serum input button 316 is provided for selecting the kind of the samples of the cup set positions 1 to 10 selected by the cursor 350. For example, when a sample is whole blood, the "WB" is displayed; when a sample is serum, the "S" is displayed. The contents registered by the above various buttons are reflected on the order list display section 318.

Figure 24:
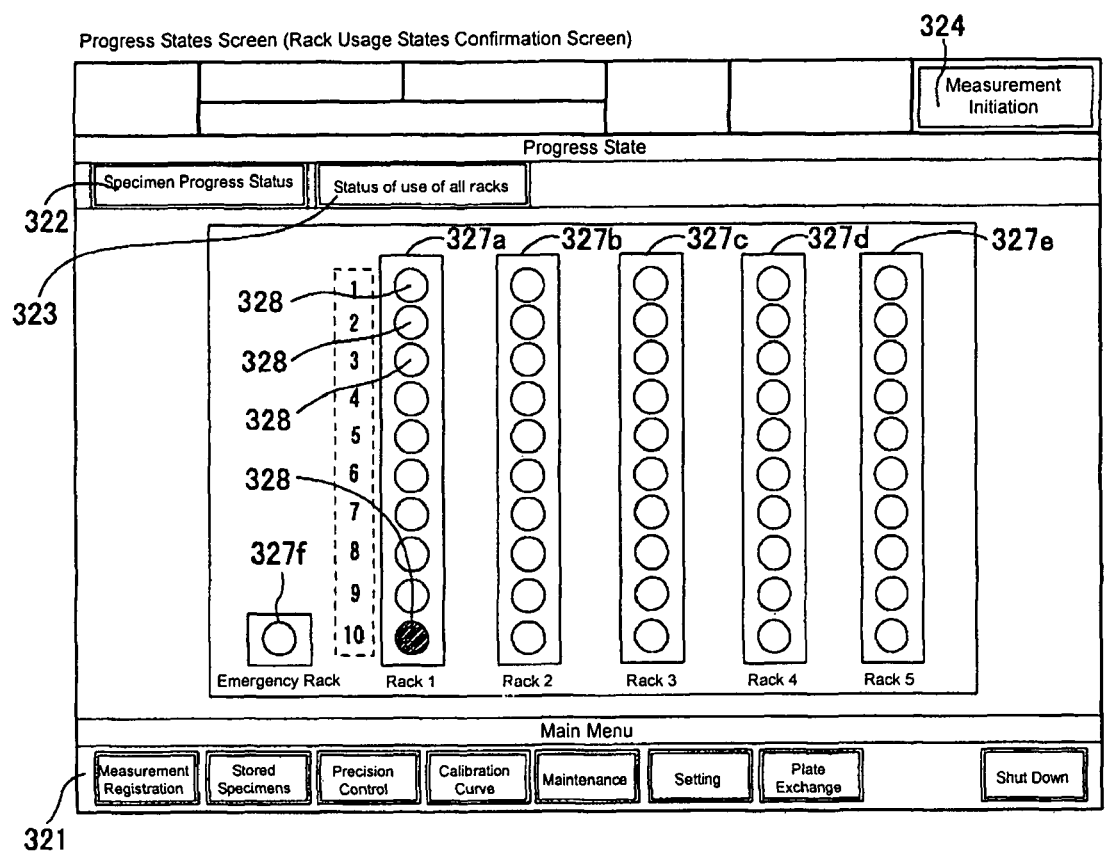
FIG. 24 is a diagram indicating a progress status screen (rack usage status confirmation screen) displayed on a display section of the immune aggregation measurement apparatus according to the embodiment indicated in FIG. 16.

On the progress status screen are displayed, as shown in FIGS. 23 and 24, a main menu section 321 having disposed therein a button that causes the measurement registration screen (see FIG. 22) and the like to be displayed, a specimen progress status display button 322 that causes a specimen progress status confirmation screen indicated in FIG. 23 to be displayed, an all-rack usage status display button 323 that causes the rack usage status confirmation display indicated in FIG. 24 to be displayed, and a measurement initiation button 324.

If a user touches the specimen progress status display button 322 indicated in FIGS. 23 and 24, as shown in FIG. 23, the specimen progress status confirmation screen is displayed. On the specimen progress status confirmation screen are displayed five rack designation buttons 325a to 325e and one emergency specimen rack designation button 325f, and a measurement result display section 326 displaying the measurement results of samples and the precision control sample.

The five rack designation buttons 325a to 325e have a function similar to the function of the rack designation buttons 311a to 311e on the measurement registration screen (see FIG. 22), and are disposed for designating a predetermined rack 231 of the specimen holder section 230. For example, if a user touches the rack designation button 325a (on the screen, "rack 1 in measurement", a rack 231 mounted on the specimen holder 230a of the specimen holder section 230 (see FIG. 19) is designated. As a result, on the measurement result display section 326 are displayed the measurement results of samples within 10 sample cups 202 mounted on the rack 231 of the specimen holder 230a and the precision control sample. In addition, the emergency specimen rack designation button 325f designates the emergency specimen holder 230f of the specimen holder section 230. If a user touches the emergency specimen rack designation button 325f, a rack 231 mounted on the emergency specimen holder 230f of the specimen holder section 230 (see FIGS. 17 and 19) is designated. As a result, on the measurement result display section 326 is displayed the measurement result of the emergency specimen sample.

On the measurement result display section 326 are disposed a sample position display column 326a, sample ID display column 326b, whole blood and serum display column 326c, and result display column 326d displaying measurement results (concentrations, flags, and so forth) in each entry for measurement. On this measurement result display section 326 are displayed sample IDs and measurement results about a rack 231 designated by touching the rack designation buttons 325a to 325e and the emergency specimen rack designation button 325f as described above. In this embodiment, a screen is displayed when the rack designation button 325a for designating the rack 231 of the specimen holder 230a is touched.

On the sample ID display column 326b are displayed sample IDs corresponding to the cup set positions 1 to 10 displayed on the sample position display column 326a. This sample ID is inputted on the measurement registration screen (see FIG. 22) in advance. On the whole blood/serum display column 326c are displayed the kinds of samples (e.g., whole blood: "WB", serum: "S") registered using the whole blood and serum input button 316 of the measurement registration screen. On the result display column 326d are displayed the concentrations (ng/ml) of samples (on the screen, ">56.00" and "1.30/+" and so forth) calculated from the intensities of scattered light detected by the optical detection section 270 as described above. This sample concentration is calculated by substituting the degree of aggregation of latex particles (see FIG. 20) calculated from the intensity of scattered light obtained by the optical detection section 270 (see FIG. 21) into a calibration curve (see FIG. 25) that is a function of a calibrator concentration constructed by a calibrator measured in advance and the degree of aggregation of a calibrator.

If a user touches the all-rack usage status display button 323 indicated in FIG. 23, the specimen progress status confirmation screen is replaced by the rack usage status confirmation screen capable of confirming the usage status of the rack 231. On the rack usage status confirmation screen are provided, as shown in FIG. 24, rack display sections 327a to 327e for displaying the conditions of the sample cups 202 mounted on the respective racks 231 of the specimen holders 230a to 230e, and an emergency specimen rack display section 327f for displaying the conditions of the sample cup 202 mounted on the rack 231 of the emergency specimen holder 230f. The rack display sections 327a to 327e each include 10 sample cup display sections 328, which have functions of displaying the conditions of order registration of samples and a precision control sample within the sample cup 202. For the measurement conditions of samples and a precision control sample, when the order is not registered, the sample cup display section 328 is displayed in white. When the order is registered, the sample cup display section 328 is displayed in green. During measurement of the sample and precision control sample, the sample cup display section 328 is displayed in red. FIG. 24 shows a case where the sample of the cup set position 10 of the rack set position 1 is during measurement, and a case where the sample cup display section 328 of the cup set position 10 of the rack set position 1 is displayed in red. Moreover, FIG. 24 shows the case where the samples with the exception of the sample of the cup set position 10 of the rack set position 1 are already registered, and the case where the sample cup display sections 328 with the exception of the display section of the cup set position 10 of the rack set position 1 are displayed in green.

Figure 26:
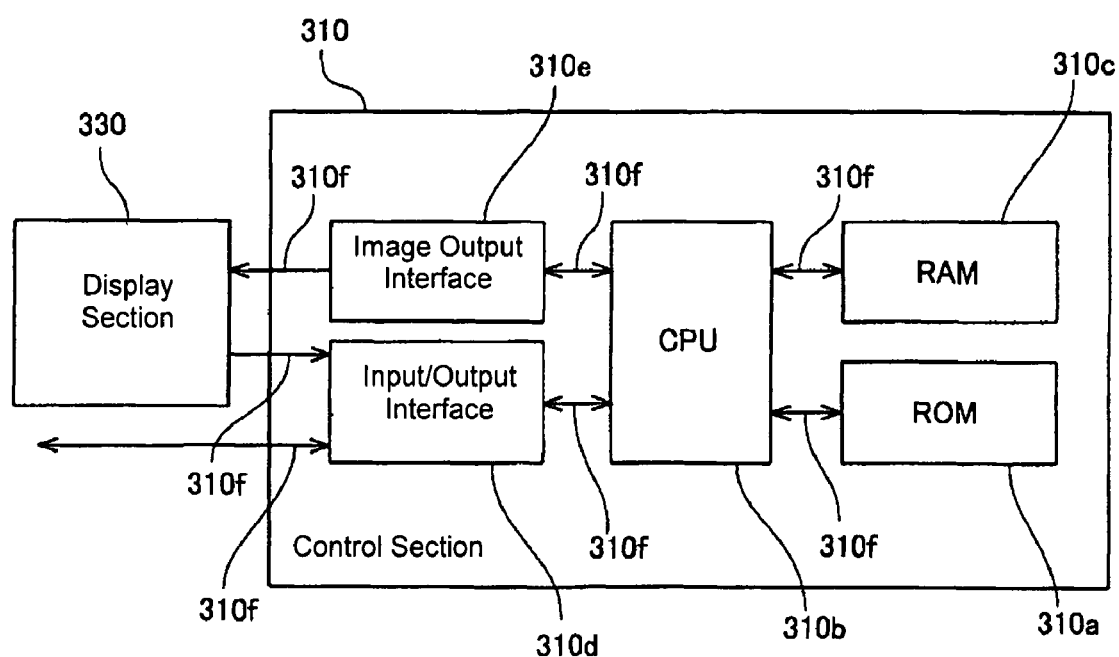
FIG. 26 is a block diagram of the control section of the immune aggregation measurement apparatus according to the embodiment indicated in FIG. 16.

Next, the control section 310 will be set forth in detail with reference to FIGS. 21, 22, and 26. The control section 310 comprises, as shown in FIG. 26, a ROM 310a, CPU 310b, RAM 310c, input/output interface 310d and image output interface 310e; they are connected to each other by the bus 310f in a communication possible fashion.

The CPU 310b has a function of executing a computer program stored in the ROM 310a or RAM 310c. By the execution of the computer program in this manner, the CPU 310b performs processing such as calculating the concentration of the antigens within a sample from the intensity of scattered light detected by the optical detection section 270 (see FIG. 21), and the like.

The RAM 310c is used as an operation region of the UPU 310b. Specifically, the RAM 310c is used as an operation region when the CPU 310b calculates the degree of aggregation or a concentration from the intensity of scattered light detected in the optical detection section 270.

The input and output interface 310d comprises, for example, serial interfaces such as a USB, IEEE 1394 and RS-232C, parallel interfaces such as an SCSI, IDE and IEEE 1284, and analog interfaces comprised of a D/A converter, A/D converter and others, and the like. To this input and output interface 310d is connected a display section 330 comprised of a touch panel, and the interface is configured so that a given input data is outputted to the CPU 310b if a user touches the display section 330 comprised of a touch panel. Additionally, The image output interface 310e is connected to the display section 330, and is configured so that a video signal corresponding to an image data given from the CPU 310b is outputted to the display section 330.

Next, the operation of the immune aggregation measurement apparatus 200 according to the embodiment will be set forth in reference with FIGS. 16 to 24 and 27. The immune aggregation measurement apparatus 200 according to the embodiment involves, as discussed above, aggregating latex particles holding antibodies bonding to antigens in blood (sample), calculating the degree of aggregation by irradiating aggregation lumps of aggregated latex particles with light, and then measuring the concentration of the antigens in the blood (sample) from its aggregation degree.

First, as shown in FIG. 19, sample cups 202 containing whole blood or serum (sample) are set to the rack 231 of the specimen holders 230a to 230e. Prior to the initiation of measurement, the order registrations such as sample IDs and the dilution ratio of samples are carried out on the measurement registration screen (see FIG. 22) using various buttons displayed on the display section 330 (touch panel) illustrated in FIGS. 16 and 17. This stores, in this embodiment, the positions of samples in the ROM 310a of the control section 310.

Then, when a user touches the measurement initiation button 319 (see FIG. 22) or 324 (see FIGS. 23 and 24), the measurement operation of the immune aggregation measurement apparatus 200 is started. When the operation of the immune aggregation measurement apparatus 200 is started, first, the unused reaction plate 201 is transported to the reaction section 240 from the reaction plate tray 280 by means of the plate catcher section 212 of the dispensing section 210 indicated in FIG. 18.

Thereafter, the CPU 310b of the control section 310 of the immune aggregation measurement apparatus 200 decides whether or not the order registration of a sample is present. If the CPU 310b decides the presence of the order registration of a sample, it controls the dispensing section 210 so as to dividedly pour a sample within the sample cup 202. Then, the concentration of this sample is measured in the measurement process in accordance with the flow chart illustrated in FIG. 27 as discussed later.

Figure 27:
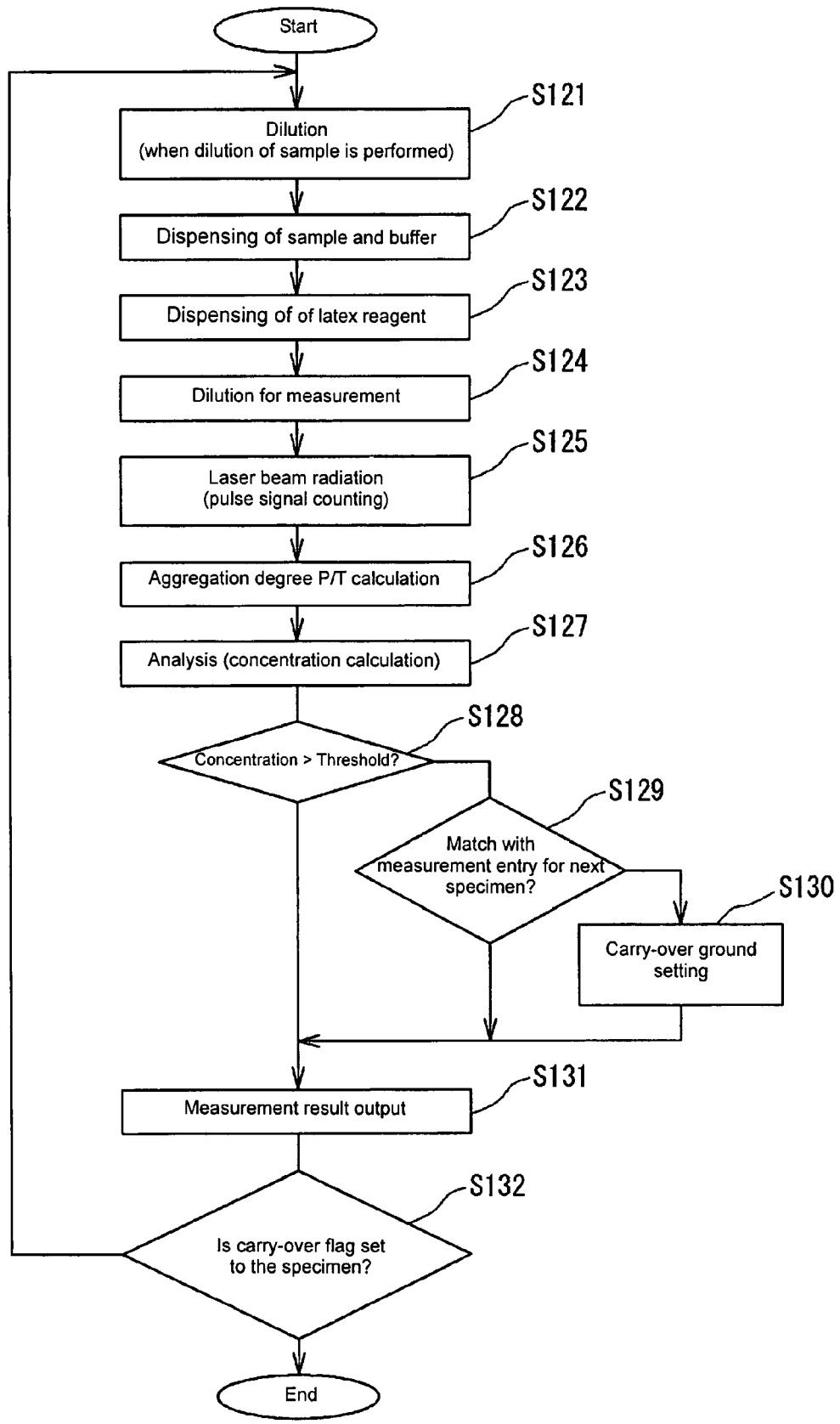
FIG. 27 is a flow chart indicating the measurement process of the immune aggregation measurement apparatus according to the embodiment indicated in FIG. 16.

Next, the measurement process will be set forth in detail with reference to FIG. 27. FIG. 27 is a flow chart indicating the measurement process of the immune aggregation measurement apparatus illustrated in FIG. 16. First, as illustrated in FIG. 27, in Step S121, when a sample of the sample cup 202 is diluted (when the dilution ratio registered in the measurement registration screen exceeds one time), specimen and latex pipette section 211 of the dispensing section 210 is moved to the specimen dilution solution vessel set section 223 of the reagent placement section 220, for suction of the specimen dilution solution. Then, the specimen and latex pipette section 211 sucks the sample from the sample cup 202 after sucking the specimen dilution solution. Thereafter, the specimen and latex pipette section 211 ejects the specimen dilution solution and the samples that are sucked to the cuvette 201a of the reaction plate 201 set in the reaction section 240. This prepares the dilution specimen in the cuvette 201a of the reaction plate 201. Additionally, when a sample is not diluted (when the dilution ratio registered in the measurement registration screen is equal to one), the above step is omitted.

In Step S122, the specimen and latex pipette section 211 of the dispensing section 210 is moved to the buffer vessel set section 221 of the reagent placement section 220 after ejecting the dilution specimen (specimen dilution solution and samples). Then, the specimen and latex pipette section 211, after sucking a buffer, is moved to the cuvette 201a containing the dilution solution, sucks the diluted specimen within the cuvette 201a, and then ejects the buffer and diluted specimen to the other cuvette 201a of the reaction plate 201. Additionally, for a non-diluted specimen not preparing a diluted specimen (when the dilution ratio registered in the measurement registration screen is equal to one), the specimen and latex pipette section 211 is moved to the sample cup 202 after sucking the buffer, sucks a sample within the sample cup 202, and then ejects the buffer and the sample to the cuvette 201a of the reaction plate 201.

Thereafter, in Step S123, about 80 seconds after the diluted specimen or the non-diluted specimen and the buffer are dividedly poured, the specimen and latex pipette section 211 of the dispensing section 210 is moved to the latex reagent vessel set section 222 of the reagent placement section 220. Then, the specimen and latex pipette section 211 sucks the latex reagent, and subsequently is moved to the cuvette 201a containing the diluted specimen or the non-diluted specimen and the buffer to eject the latex reagent into the cuvette 201a. This binds, as shown in FIG. 20, the antigens in the sample to the antibodies bonding to the latex particles within the latex reagent and initiates the aggregation reaction of the latex particles.

Next, in Step S124, about 20 seconds and about 15 minutes after the latex reagent is dividedly poured, the measurement dilution pipette section 251 of the measurement dilution dispensing section 250 is moved to the cuvette 201a where the latex reagent is ejected. Then the measurement dilution pipette section 251 sucks a prepared sample within its cuvette 201a (sample, buffer and latex reagent), and then moves to the sample receptive section 260 (see FIG. 18) to eject the prepared sample into the sample receptive section 260. At this time, the measurement dilution dispensing section 250 ejects a measurement dilution solution accommodated in a tank (not shown) placed in a lower part of the immune aggregation measurement apparatus 200 to the sample receptive section 260, together with the prepared sample. Thereafter, on the prepared samples about 20 seconds and about 15 minutes after the latex reagent is dividedly poured are carried out Steps S125 to S130 as discussed later to obtain the degree of aggregation of the prepared sample after about 20 seconds (T1 measurement result) and the degree of aggregation of the prepared sample after about 15 minutes (T2 measurement result). The analyses of these T1 and T2 measurement results lead to the implementation of calculation of the concentration.

In such a processing flow of a specimen, processing is carried out in order from the measurement entry in which a sample of the position 1 of the rack 1 is measurement registered. The measurement registration of FIG. 22 involves, first, dividedly pouring a diluted specimen or non-diluted specimen and a buffer for measurement of the HBsAg of the sample of the specimen number 121, then for every 30 seconds, dividedly pouring the diluted specimen, non-diluted specimen and buffer in order listed, for the measurements of the HCV of the sample of the specimen number 121, of the TP of the sample of the specimen number 222, of the HCV of the sample of the specimen number 222 and of the CEA of the precision control sample of the specimen number QC01. Thereafter, for every such measurement entry of each specimen, after dispensing of the diluted specimen or non-diluted specimen and the buffer, the dispensing of the latex reagent, dilution for measurement, and measurements (irradiation with a laser beam and pulse signal counting, calculation of aggregation degree P/T, analysis, output of measurement results) are implemented. In other words, a plurality of these processing operations are overlapped for 30 seconds.

Figure 28:
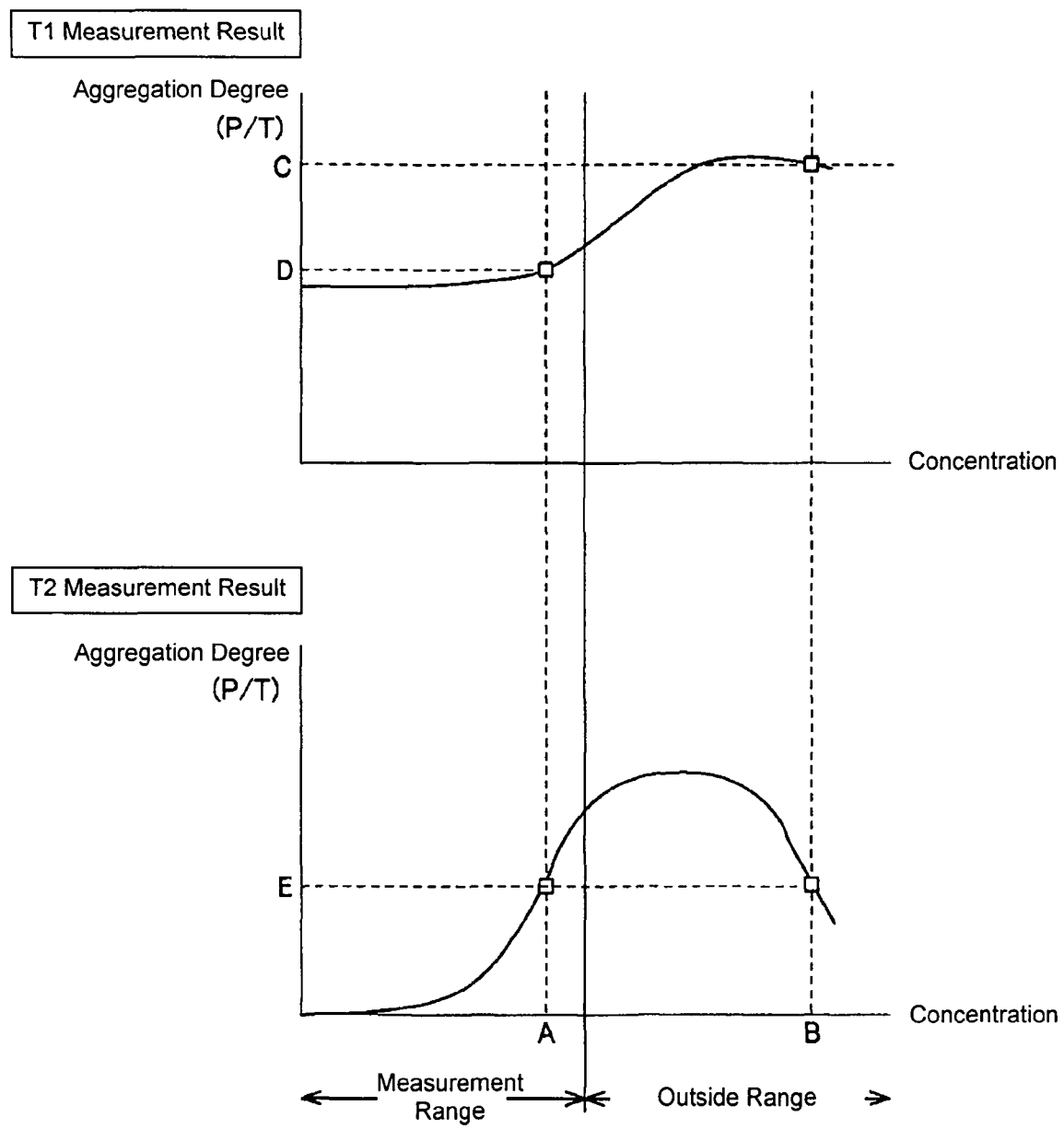
FIG. 28 is a graph indicating the relationship between the degree of aggregation and concentration of the T1 and T2 measurement results.

FIG. 28 is a graph indicating the relationship between the degree of aggregation and concentration of the T1 and T2 measurement results. When the concentration of antigens of a sample is high, as shown in the graph of the T2 measurement result in FIG. 28, the aggregation of latex particles is sometimes weak, and an appropriate concentration may not be calculated from the degree of aggregation. For this reason, in this embodiment, when the T1 and T2 measurement results as discussed above are obtained, if the T2 measurement result (aggregation degree) is E, a decision is made on the basis of the T1 measurement result (aggregation degree) so as not to obtain an inappropriate concentration attributable to weakening of the aggregation of latex particles. Specifically, if the T2 measurement result (aggregation degree) is E and the T1 measurement result (aggregation degree) is D, the concentration A corresponding to the T1 measurement result is within the range of measurement, so the concentration is calculated from the T2 measurement result (aggregation degree). On the contrary, if the T2 measurement result (aggregation degree) is E and the T1 measurement result (aggregation degree) is C, the concentration B corresponding to the T1 measurement result is out of the range of measurement (outside range), so if the concentration is calculated from the T2 measurement result (aggregation degree) in the usual manner, an appropriate concentration is not sometimes calculated. Therefore, if the concentration B corresponding to the T1 measurement result is out of the measurement range (outside range), the dilution ratio of a sample is changed and measurement is performed again.

Thereafter, in Step S125, a particle suspension solution (the prepared sample and measurement dilution solution) ejected into the sample receptive section 260 (see FIG. 18) is guided and converted into a flat flow by the sheath flow cell 274 of the optical detection section 270 (see FIG. 21). In this state, an aggregation lump of latex particles flowing through the sheath flow cell 274 is irradiated with a laser beam having a wavelength of about 780 nm from the laser diode 271 (see FIG. 21), and a plurality of scattered light beams having intensities depending on the sizes of the aggregated lumps of the latex particles are received in the photodiode 275 (see FIG. 21). At this time, the CPU 310*b* of the control section 310 (see FIG. 26) counts each of the scattered light beams received in the photodiode 275 as a pulse signal.

Then in Step S126, the CPU 310*b* (see FIG. 26) classifies the latex particles into non-aggregated latex particles and aggregated latex particles based on the intensities of the scattered light beams received as pulse signals to calculate the degree of aggregation. Specifically, the CPU 310*b*, when the intensity of a received scattered light beam is a predetermined magnitude or larger, decides the aggregated lump of latex particles that generates the scattered light beam to be a polymer (P) (aggregated latex particles), and the aggregated lump of latex particles that generates the scattered light beam to be a monomer (M) (non-aggregated latex particles) when the intensity of a received scattered light beam is less than a predetermined magnitude. Then, the CPU 310*b* calculates the degree of aggregation P/T of the latex particles from Equation (1) indicated below, using the number of counts P of scattered light beams equal to or larger than a predetermined magnitude and the number of counts M of scattered light beams smaller than the predetermined magnitude.

$$P/T=P/(P+M) \tag{1}$$

Figure 25:
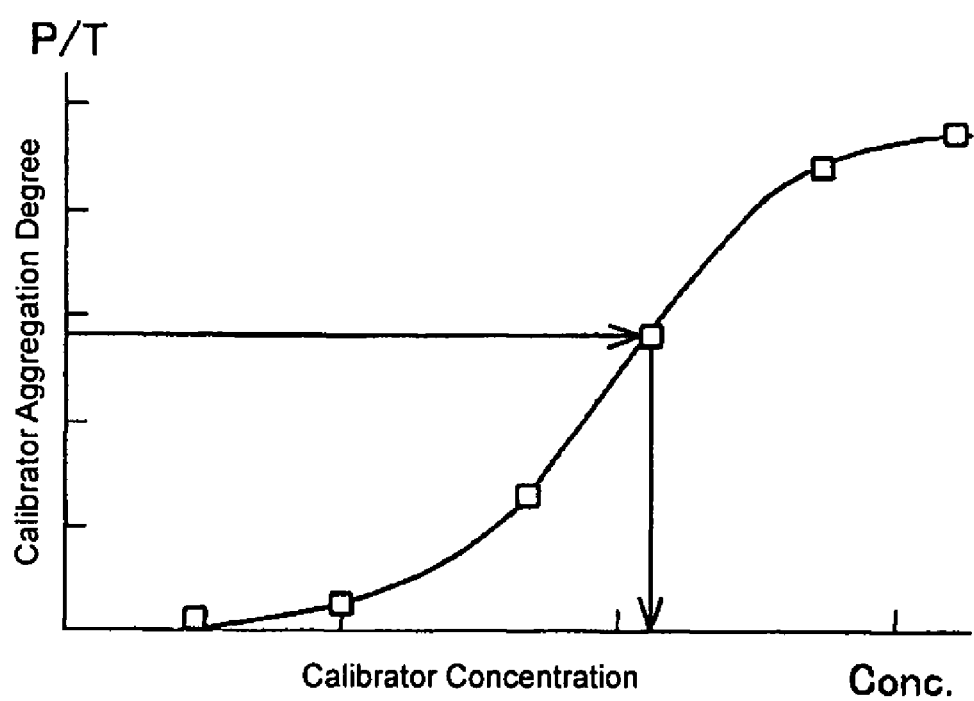
FIG. 25 is a graph in which a calibration curve is drawn that indicates the relationship between the concentration and the degree of aggregation of a carburetor used in the immune aggregation measurement apparatus according to the embodiment indicated in FIG. 16.

In Step S127, the CPU 310*b* converts the degree of aggregation P/T into the concentration using a calculated aggregation degree P/T and a calibration curve constructed in advance (see FIG. 25). Next, in Step S128, the CPU 310*b* decides whether or not the calculated concentration is larger than a predetermined threshold. This threshold is set in advance for every measurement entry. This threshold is for deciding whether or not a sample is an extremely high value specimen. If the concentration is larger than the threshold, the specimen can be decided to be an extremely high value specimen.

In immune aggregation measurement, if the previous sample is a high value specimen, and when a next sample is affected by carry-over, only the same measurement entry is affected. In other words, even if the previous sample is a high value specimen, when a measurement entry different from the measurement entry that had a high value in the previous sample is measured in the next sample, the measurement of the next sample is not substantially affected by carry-over. Thus, if the concentration is larger than the threshold in Step S128, in Step S129, the CPU 310*b* decides whether or not the measurement entry implemented this time (decided to be a high value specimen) is registered for the next sample to be measured. If the same measurement entry as this time is registered for the next sample in Step S129, in Step S130, the CPU 310*b* sets a flag for carry-over in the next sample, and stores this flag in the RAM 310*c*.

If the concentration is equal to or less than the threshold in Step S128 and if the same measurement entry as this time is not registered for the next sample in Step S129 or if a flag for carry-over is set for the next sample in Step S130, in Step S131, the CPU 310*b* displays, as shown in FIG. 23, an obtained concentration on the display section 330 as well as renders the RAM 310*c* to correspond a position of the sample cup 202 of the detection holder section 230 (the cup set position 1 of the rack set position 1) to the concentration and store the concentration. Next, in Step S132, the CPU 310*b* decides whether or not a flag for carry-over is set for the measurement entry of the sample measured this time. Namely, in Step S131, the CPU 310*b* decides whether or not a high value is outputted in the same measurement entry as the measurement entry this time in the sample prior to the sample measured this time, i.e., decides whether or not the measurement result this time is affected by the carry-over of the previous specimen. Then, if a flag for carry-over is not set, the CPU 310*b* causes the cleaning section to clean the dispensing section 210 and the measurement dilution pipette section 251 of the measurement dilution dispensing section 250, and completes the processing; if a flag for carry-over is set, the CPU 310*b* causes the cleaning section to clean the dispensing section 210 and the measurement dilution pipette section 251 of the measurement dilution dispensing section 250, and subsequently returns the processing to Step S121 and causes the re-processing of the sample this time to be implemented.

If the measurement result of HCV of a sample of the specimen number 121 indicates an extremely high value (the concentration is larger than the threshold in Step S128), the carry-over of HCV may occur in the processing of a sample of the specimen number 222 of the next specimen, and the measurement result of the HCV of the sample of the specimen number 222 may be erroneous. Hence, after a measurement result of an extremely high value follows in the HCV of the sample of the specimen number 121, the HCV of the sample of the specimen number 222 is measured again. The dispensing section 210 is moved to the position of the sample of the specimen number 222 and the sample is sucked, and then the processing operation of the specimen is carried out in the same manner as the above flow.

On the other hand, if a measurement result in HBsAg of the sample of the specimen number 121 indicates a high value, the carry-over of the HBsAs in the processing of the sample of the specimen number 222 of the next specimen may occur. However, in this case, the measurement of the HBsAG for the sample of the specimen number 222 is not performed; even if the carry-over of HBsAG in measurement of another entry occurs, the measurement result is not affected, so the sample of the specimen number 222 is not processed again.

Figure 29:
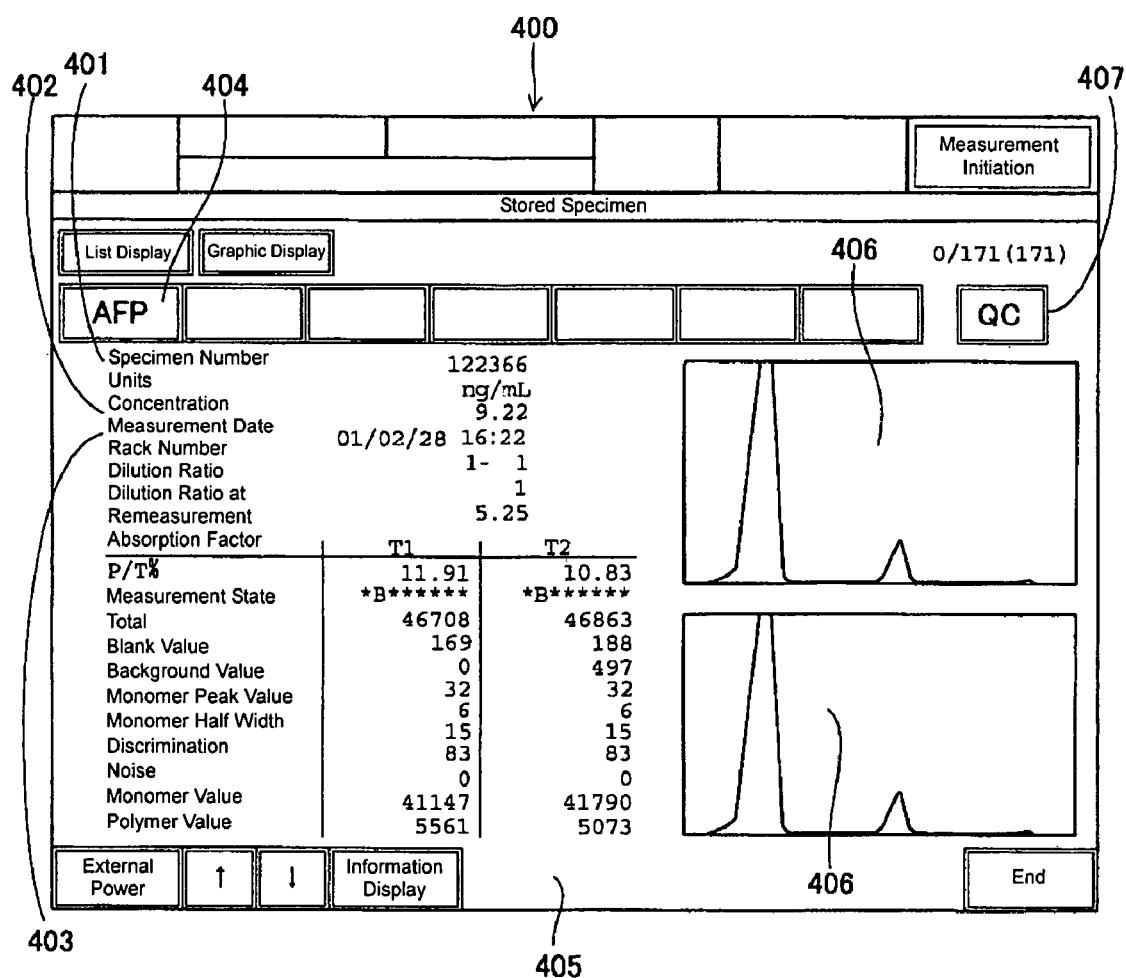
FIG. 29 is a diagram indicating a detail information screen displayed on the display of the immune aggregation measurement apparatus according to the embodiment indicated in FIG. 16.

In the immune aggregation measurement apparatus 200, detailed information of the measurement result of a sample (detailed information screen) can be displayed. The CPU 310b displays the detailed information screen of the measurement result of a measurement entry on the display section 330 when it has received the selection of the measurement result of the desired measurement entry for a user on the measurement result list display screen. FIG. 29 is a diagram indicating one example of a detailed information screen. As shown in FIG. 29, this detailed information screen 400 displays information such as the specimen number 401, a measurement result 402 and a measurement date 403, a measurement entry 404, and numerical value information 405 indicating a measurement result in detail, and also displays a measurement result in terms of a graph 406. Additionally, this detailed information screen 400 displays a carry-over flag 407 when the flag of carry-over is set. This can inform a user about the occurrence of carry-over when sample whose detailed information is displayed is influenced by carry-over. The user can be informed that this specimen needs to be measured again if the carry-over flag 407 is displayed, and can take necessary measures such as not using the measurement result.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A urine specimen analysis apparatus for analyzing a component contained in a urine specimen, comprising:
   a specimen suction section that sucks a urine specimen from a specimen vessel placed on a specimen vessel placing section;
   a sample preparation section that prepares a measurement sample from the urine specimen sucked by the specimen suction section and a reagent;
   a measurement section comprising a flow cell connected to the sample preparing section, and an optical detector that detects an optical information from the prepared measurement sample flowing through the flow cell;
   a cleaning section that cleans a sample passage channel of the sample preparation section and a sample passage channel of the measurement section; and
   a non-transitory computer readable storage medium having stored therein data representing instructions executable by a processor, the storage medium comprising:
   a first set of instructions to control operations of the specimen suction section, the sample preparation section, the measurement section and the cleaning section to implement a processing of a previous urine specimen, the processing comprising a suction of the previous urine specimen, a preparation of a previous measurement sample, a detection of an optical information from the prepared previous measurement sample and a first cleaning of sample passage channels after the detection of the optical information from the prepared previous measurement sample;
   a second set of instructions to control operations of the specimen suction section, the sample preparation section, the measurement section and the cleaning section to implement a processing of a next urine specimen, including to initiate a suction of the next urine specimen during the implementation of the processing of the previous urine specimen, to implement a preparation of a next measurement sample and a detection of an optical information from the prepared next measurement sample after the suction of the next urine specimen and to implement a first cleaning of the sample passage channels after the detection of the optical information from the prepared next measurement sample;
   a third set of instructions to obtain a bacteria number information representing a number of bacteria in the previous measurement sample based on a detection result of the previous measurement sample, and to judge whether the obtained bacteria number information exceeds a threshold;
   a fourth set of instructions to control operations of the specimen suction section, the sample preparation section, the measurement section and the cleaning section to implement a reprocessing of the next specimen when the bacteria number information of the previous measurement sample is judged to exceed the threshold; and
   a fifth set of instructions to control operations of the specimen suction section, the sample preparation section, the measurement section and the cleaning section
      to initiate, when the bacteria number information of the previous measurement sample is judged not to exceed the threshold, a processing of another urine specimen different from the previous and the next urine specimens during the implementation of the processing of the next urine specimen and
      to temporarily prevent the specimen suction section, the sample preparation section, the measurement section and the cleaning section from entering the processing of the another urine specimen until after initiation of the reprocessing of the next urine specimen, when the bacteria number information of the previous measurement sample is judged to exceed the threshold.

2. The urine specimen analysis apparatus according to claim 1, wherein
   the second set of instructions is configured to control operations of the specimen suction section, the sample preparation section, the measurement section and the cleaning section to initiate the suction of the next specimen and the preparation of the next measurement sample while the previous measurement sample is flowing through the flow cell, and to initiate the detection of the optical information from the next measurement sample after a completion of the flowing of the previous measurement sample through the flow cell.

3. The urine specimen analysis apparatus according to claim 1
   wherein the fourth set of instructions is configured so as to further control the cleaning section to implement a second cleaning of the sample passage channels different from the first cleaning of the sample passage channels after detection of the optical information from the next measurement sample and before initiation of the reprocessing of the next specimen, when the bacteria number information of the previous measurement sample is judged to exceed the threshold.

4. The urine specimen analysis apparatus according to claim 1, wherein
   the specimen vessel placing section comprises a transport mechanism for transporting specimen vessels to the specimen suction section.

5. The urine specimen analysis apparatus according to claim 4, wherein the transport mechanism is configured so as to be capable of retreating the specimen vessels to the specimen suction section.

6. The urine specimen analysis apparatus according to claim 5, wherein
the fourth set of instructions is configured so as to control the transport mechanism to retreat at least one of the specimen vessels when the bacteria number information of the previous measurement sample is judged to exceed the threshold.

7. A urine specimen analysis apparatus for analyzing a component contained in a urine specimen, comprising:
a specimen suction section that sucks a urine specimen from a specimen vessel placed on a specimen vessel placing section;
a sample preparation section that prepares a measurement sample from the urine specimen sucked by the specimen suction section and a reagent;
a measurement section comprising a flow cell connected to the sample preparing section, and an optical detector that detects an optical information from the prepared measurement sample flowing through the flow cell;
a cleaning section that cleans a sample passage channel of the sample preparation section and a sample passage channel of the measurement section;
a display; and
a non-transitory computer readable storage medium having stored therein data representing instructions executable by a processor, the storage medium comprising:
a first set of instructions to control operations of the specimen suction section, the sample preparation section, the measurement section and the cleaning section to implement a processing of a previous urine specimen, the processing comprising a suction of the previous urine specimen, a preparation of a previous measurement sample, a detection of an optical information from the prepared previous measurement sample and a cleaning of sample passage channels after the detection of the optical information from the previous measurement sample;
a second set of instructions to control operations of the specimen suction section, the sample preparation section, the measurement section and the cleaning section to implement a processing of a next urine specimen, including to initiate a suction of the next urine specimen during the implementation of the processing of the previous urine specimen, to implement a preparation of a next measurement sample and a detection of an optical information from the prepared next measurement sample after the suction of the next urine specimen, and to implement a cleaning of the sample passage channels after the detection of the optical information from the next measurement sample;
a third set of instructions to obtain a bacteria number information representing a number of bacteria in the previous measurement sample based on a detection result of the previous measurement sample, and to judge whether the obtained bacteria number information exceeds a threshold;
a fourth set of instructions to show, on the display, a notice for reprocessing of the next specimen when the bacteria number information of the previous measurement sample is judged to exceed the threshold; and
a fifth set of instructions to control operations of the specimen suction section, the sample preparation section, the measurement section and the cleaning section to initiate, when the bacteria number information of the previous measurement sample is judged not to exceed the threshold, a processing of another urine specimen different from the previous and the next urine specimens during the implementation of the processing of the next urine specimen and
to temporarily prevent the specimen suction section, the sample preparation section, the measurement section and the cleaning section from entering the processing of the another urine specimen until after initiation of the reprocessing of the next urine specimen, when the bacteria number information of the previous measurement sample is judged to exceed the threshold.

8. A urine specimen analysis apparatus for analyzing a component contained in a urine specimen, comprising:
a specimen vessel placing section on which a plurality of specimen vessels are capable of being placed;
a specimen suction section that sucks a urine specimen from a specimen vessel placed on the specimen vessel placing section;
a sample preparation section that prepares a measurement sample from the urine specimen sucked by the specimen suction section and a reagent;
a measurement section comprising a flow cell connected to the sample preparation section, and an optical detector that detects an optical information from the prepared measurement sample flowing through the flow cell;
a cleaning section that cleans a sample passage channel of the sample preparation section and a sample passage channel of the measurement section; and
a controller comprising a processor and a memory that stores programs executable by the processor to:
control operations of the specimen suction section, the sample preparation section, the measurement section and the cleaning section to implement a processing of a previous urine specimen, the processing comprising a suction of the previous urine specimen, preparation of a previous measurement sample, a detection of an optical information from the prepared previous measurement sample and a first cleaning of sample passage channels after the detection of the optical information from the prepared previous measurement sample;
control operations of the specimen suction section, the sample preparation section, the measurement section and the cleaning section to implement a processing of a next urine specimen, including to initiate a suction of the next specimen during the processing of the previous specimen, to implement a preparation of a next measurement sample and a detection of an optical information from the prepared next measurement after the suction of the next urine specimen, and to implement a first cleaning of the sample passage channels after the detection of the optical information from the next measurement sample;
obtain a bacteria number information representing a number of bacteria in the previous measurement sample based on a detection result of the previous measurement sample;
control operation of the cleaning section to implement a second cleaning of the sample passage channels different from the first cleaning of the sample passage channels after completion of the processing of the next urine specimen and before initiation of the reprocessing of the next specimen, when the bacteria number information of the previous measurement sample exceeds the threshold;

after the second cleaning of the sample passage channels, control operations of the specimen suction section, the sample preparation section, the measurement section and the cleaning section to implement a reprocessing of the next urine specimen.

9. A urine specimen analysis apparatus for analyzing a component contained in a urine specimen, comprising:
- a specimen vessel placing section on which a plurality of specimen vessels are capable of being placed;
- a specimen suction section that sucks a urine specimen from a specimen vessel placed on the specimen vessel placing section;
- a sample preparation section that prepares a measurement sample from the urine specimen sucked by the specimen suction section and a reagent;
- a measurement section comprising a flow cell connected to the sample preparing section, and an optical detector that detects an optical information from the prepared measurement sample flowing through the flow cell;
- a cleaning section that cleans a sample passage channel of the sample preparation section and a sample passage channel of the measurement section;
- a display; and
- a controller comprising a processor and a memory that stores programs executable by the processor to:
- control operations of the specimen suction section, the sample preparation section, the measurement section and the cleaning section to implement a processing of a previous specimen, the processing comprising a suction of the previous specimen, a preparation of a previous measurement sample, a detection of an optical information from the prepared previous measurement sample and a first cleaning of sample passage channels after the detection of the optical information from the previous measurement sample;
- control operations of the specimen suction section, the sample preparation section, the measurement section and the cleaning section to implement a processing of a next urine specimen, including to initiate a suction of the next specimen during the processing of the previous specimen, to implement a preparation of a next measurement sample and a detection of an optical information from the prepared next measurement after the suction of the next urine specimen, and to implement a first cleaning of the sample passage channels after the detection of the optical information from the next measurement sample;
- obtain a bacteria number information representing a number of bacteria in the previous measurement sample based on a detection result of the previous measurement sample;
- show, on the display, a notice for reprocessing of the next urine specimen when the bacteria number information of the previous measurement sample exceeds a threshold;
- control the cleaning section to implement a second cleaning of the sample passage channels different from the first cleaning of the sample passage channels after completion of the processing of the next urine specimen and before initiation of the reprocessing of the next specimen, when the bacteria number information of the previous measurement sample exceeds the threshold; and
- after the second cleaning of the sample passage channels, control operations of the specimen suction section, the sample preparation section, the measurement section and the cleaning section to implement a reprocessing of the next urine specimen.

* * * * *